United States Patent
Rodriguez-Suarez et al.

(10) Patent No.: US 8,323,919 B2
(45) Date of Patent: Dec. 4, 2012

(54) ASSAY METHODS FOR IDENTIFYING GLYCOGEN SYNTHASE KINASE 3 MODULATORS

(75) Inventors: Roberto J. Rodriguez-Suarez, Saint-Laurent (CA); Lucille Beaudet, Varennes (CA); Mireille Caron, Blainville (CA)

(73) Assignee: PerkinElmer BioSignal, Inc., Montreal, Quebec (CA)

( * ) Notice: Subject to any disclaimer, the term of this patent is extended or adjusted under 35 U.S.C. 154(b) by 0 days.

(21) Appl. No.: 12/892,615

(22) Filed: Sep. 28, 2010

(65) Prior Publication Data

US 2011/0081659 A1     Apr. 7, 2011

Related U.S. Application Data

(60) Provisional application No. 61/246,468, filed on Sep. 28, 2009.

(51) Int. Cl.
    *C12Q 1/48*     (2006.01)
(52) U.S. Cl. .......................................... 435/15
(58) Field of Classification Search ........................ None
    See application file for complete search history.

(56) References Cited

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Funai et al, Age-associated decrease in contraction-induced activation of downstream targets of Akt/mTor signaling in skeletal muscle. Am J Physiol Regul Integr Comp Physiol. Apr. 2006;290(4):R1080-6. Epub Nov. 23, 2005.*
Rayasam, G, "Glycogen synthase kinase 3: more than a namesake," *British Journal of Pharmacology*, 156: 885-898, 2009.
Doble, B., "GSK-3: tricks of the trade for a multi-tasking kinase," *J Cell Sci.*, 116(Pt 7): 1175-1186, Apr. 1, 2003.

* cited by examiner

*Primary Examiner* — Sheridan Swope
(74) *Attorney, Agent, or Firm* — Gifford, Krass, Sprinkle, Anderson & Citkowski, P.C.

(57) ABSTRACT

Methods and compositions for glycogen synthase kinase 3 assays continue to be required for detection of glycogen synthase 3 kinase, assessment of glycogen synthase 3 kinase activity and identification of modulators of glycogen synthase 3 kinase. Methods and compositions for glycogen synthase kinase 3 assays are provided herein based on the discovery of a previously unknown interaction between glycogen synthase 3 kinase and eukaryotic translation initiation factor 4E-binding protein 1 which serves as a substrate for glycogen synthase kinase 3-alpha and glycogen synthase kinase 3-beta.

4 Claims, 3 Drawing Sheets

SEQUENCE LISTING

```
<160> NUMBER OF SEQ ID NOS: 9

<210> SEQ ID NO 1
<211> LENGTH: 483
<212> TYPE: PRT
<213> ORGANISM: Homo sapiens

<400> SEQUENCE: 1

Met Ser Gly Gly Gly Pro Ser Gly Gly Gly Pro Gly Gly Ser Gly Arg
1               5                   10                  15

Ala Arg Thr Ser Ser Phe Ala Glu Pro Gly Gly Gly Gly Gly Gly Gly
            20                  25                  30

Gly Gly Gly Pro Gly Gly Ser Ala Ser Gly Pro Gly Gly Thr Gly Gly
        35                  40                  45

Gly Lys Ala Ser Val Gly Ala Met Gly Gly Gly Val Gly Ala Ser Ser
    50                  55                  60

Ser Gly Gly Gly Pro Gly Gly Ser Gly Gly Gly Ser Gly Gly Pro
65                  70                  75                  80

Gly Ala Gly Thr Ser Phe Pro Pro Pro Gly Val Lys Leu Gly Arg Asp
                85                  90                  95

Ser Gly Lys Val Thr Thr Val Val Ala Thr Leu Gly Gln Gly Pro Glu
            100                 105                 110

Arg Ser Gln Glu Val Ala Tyr Thr Asp Ile Lys Val Ile Gly Asn Gly
        115                 120                 125

Ser Phe Gly Val Val Tyr Gln Ala Arg Leu Ala Glu Thr Arg Glu Leu
```

```
              130                 135                 140
Val Ala Ile Lys Lys Val Leu Gln Asp Lys Arg Phe Lys Asn Arg Glu
145                 150                 155                 160

Leu Gln Ile Met Arg Lys Leu Asp His Cys Asn Ile Val Arg Leu Arg
                165                 170                 175

Tyr Phe Phe Tyr Ser Ser Gly Glu Lys Lys Asp Glu Leu Tyr Leu Asn
                180                 185                 190

Leu Val Leu Glu Tyr Val Pro Glu Thr Val Tyr Arg Val Ala Arg His
                195                 200                 205

Phe Thr Lys Ala Lys Leu Thr Ile Pro Ile Leu Tyr Val Lys Val Tyr
210                 215                 220

Met Tyr Gln Leu Phe Arg Ser Leu Ala Tyr Ile His Ser Gln Gly Val
225                 230                 235                 240

Cys His Arg Asp Ile Lys Pro Gln Asn Leu Leu Val Asp Pro Asp Thr
                245                 250                 255

Ala Val Leu Lys Leu Cys Asp Phe Gly Ser Ala Lys Gln Leu Val Arg
                260                 265                 270

Gly Glu Pro Asn Val Ser Tyr Ile Cys Ser Arg Tyr Tyr Arg Ala Pro
                275                 280                 285

Glu Leu Ile Phe Gly Ala Thr Asp Tyr Thr Ser Ser Ile Asp Val Trp
                290                 295                 300

Ser Ala Gly Cys Val Leu Ala Glu Leu Leu Leu Gly Gln Pro Ile Phe
305                 310                 315                 320

Pro Gly Asp Ser Gly Val Asp Gln Leu Val Glu Ile Ile Lys Val Leu
                325                 330                 335

Gly Thr Pro Thr Arg Glu Gln Ile Arg Glu Met Asn Pro Asn Tyr Thr
                340                 345                 350

Glu Phe Lys Phe Pro Gln Ile Lys Ala His Pro Trp Thr Lys Val Phe
                355                 360                 365

Lys Ser Arg Thr Pro Pro Glu Ala Ile Ala Leu Cys Ser Ser Leu Leu
                370                 375                 380

Glu Tyr Thr Pro Ser Ser Arg Leu Ser Pro Leu Glu Ala Cys Ala His
385                 390                 395                 400

Ser Phe Phe Asp Glu Leu Arg Cys Leu Gly Thr Gln Leu Pro Asn Asn
                405                 410                 415

Arg Pro Leu Pro Pro Leu Phe Asn Phe Ser Ala Gly Glu Leu Ser Ile
                420                 425                 430

Gln Pro Ser Leu Asn Ala Ile Leu Ile Pro Pro His Leu Arg Ser Pro
                435                 440                 445

Ala Gly Thr Thr Thr Leu Thr Pro Ser Ser Gln Ala Leu Thr Glu Thr
                450                 455                 460

Pro Thr Ser Ser Asp Trp Gln Ser Thr Asp Ala Thr Pro Thr Leu Thr
465                 470                 475                 480

Asn Ser Ser

<210> SEQ ID NO 2
<211> LENGTH: 1451
<212> TYPE: DNA
<213> ORGANISM: Homo sapiens

<400> SEQUENCE: 2
atgagcggcg gcgggccttc gggaggcggc cctgggggct cgggcagggc gcggactagc       60
tcgttcgcgg gcccggcggc ggaggcggag gaggcggcgg cggccccgga ggctcggcct      120
ccggcccagg cggcaccggc ggcggaaagg catctgtcgg ggccatgggt ggggcgtcg       180
```

```
gggcctcgag ctccgggggt ggacccggcg gcagcggcgg aggaggcagc ggaggccccg      240
gcgcaggcac tagcttcccg ccgcccgggg tgaagctggg ccgtgacagc gggaaggtga      300
ccacagtcgt agccactcta ggccaaggcc cagagcgctc caagaagtg gcttacacgg       360 acatcaaagt gattggcaat ggctcatttg gggtcgtgta ccaggcacgg ctggcagaga      420
ccagggaact agtcgccatc aagaaggttc tccaggacaa gaggttcaag aaccgagagc      480
tgcagatcat gcgtaagctg gaccactgca atattgtgag gctgagatac ttttctact      540 ccagtggcga agaaaagac gagctttacc taaatctggt gctggaatat gtgcccgaga       600
cagtgtaccg ggtggcccgc cacttcacca aggccaagtt gaccatccct atcctctatg      660
tcaaggtgta catgtaccag ctcttccgca gcttggccta catccactcc cagggcgtgt      720
gtcaccgcga catcaagccc cagaacctgc tggtggaccc tgacactgct gtcctcaagc      780
tctgcgattt tggcagtgca aagcagttgg tccgagggga gcccaatgtc tcctacatct      840
gttctcgcta ctaccgggcc ccagagctca tctttggagc cactgattac acctcatcca      900
tcgatgtttg gtcagctggc tgtgtactgg cagagctcct cttgggccag cccatcttcc      960
ctggggacag tggggtggac cagctggtgg agatcatcaa ggtgctggga acaccaaccc     1020
gggaacaaat ccgagagatg aaccccaact acacggagtt caagttccct cagattaaag     1080
ctcacccctg gacaaaggtg ttcaaatctc gaacgccgcc agaggccatc gcgctctgct     1140
ctagcctgct ggagtacacc ccatcctcaa ggctctcccc actagaggcc tgtgcgcaca     1200
gcttctttga tgaactgcga tgtctgggaa cccagctgcc taacaaccgc ccacttcccc     1260
ctctcttcaa cttcagtgct ggtgaactct ccatccaacc gtctctcaac gccattctta     1320
tccctcctca cttgaggtcc ccagcgggca ctaccaccct caccccgtcc tcacaagctt     1380
taactgagac tccgaccagc tcagactggc agtcgaccga tgccacacct accctcacta     1440
actcctcctg a                                                         1451
```

<210> SEQ ID NO 3
<211> LENGTH: 420
<212> TYPE: PRT
<213> ORGANISM: Homo sapiens

<400> SEQUENCE: 3

```
Met Ser Gly Arg Pro Arg Thr Thr Ser Phe Ala Glu Ser Cys Lys Pro
1               5                   10                  15

Val Gln Gln Pro Ser Ala Phe Gly Ser Met Lys Val Ser Arg Asp Lys
            20                  25                  30

Asp Gly Ser Lys Val Thr Thr Val Ala Thr Pro Gly Gln Gly Pro
        35                  40                  45

Asp Arg Pro Gln Glu Val Ser Tyr Thr Asp Thr Lys Val Ile Gly Asn
    50                  55                  60

Gly Ser Phe Gly Val Val Tyr Gln Ala Lys Leu Cys Asp Ser Gly Glu
65                  70                  75                  80

Leu Val Ala Ile Lys Lys Val Leu Gln Asp Lys Arg Phe Lys Asn Arg
                85                  90                  95

Glu Leu Gln Ile Met Arg Lys Leu Asp His Cys Asn Ile Val Arg Leu
            100                 105                 110

Arg Tyr Phe Phe Tyr Ser Ser Gly Glu Lys Lys Asp Glu Val Tyr Leu
        115                 120                 125

Asn Leu Val Leu Asp Tyr Val Pro Glu Thr Val Tyr Arg Val Ala Arg
    130                 135                 140
```

-continued

```
His Tyr Ser Arg Ala Lys Gln Thr Leu Pro Val Ile Tyr Val Lys Leu
145                 150                 155                 160

Tyr Met Tyr Gln Leu Phe Arg Ser Leu Ala Tyr Ile His Ser Phe Gly
                165                 170                 175

Ile Cys His Arg Asp Ile Lys Pro Gln Asn Leu Leu Leu Asp Pro Asp
            180                 185                 190

Thr Ala Val Leu Lys Leu Cys Asp Phe Gly Ser Ala Lys Gln Leu Val
        195                 200                 205

Arg Gly Glu Pro Asn Val Ser Tyr Ile Cys Ser Arg Tyr Tyr Arg Ala
210                 215                 220

Pro Glu Leu Ile Phe Gly Ala Thr Asp Tyr Thr Ser Ser Ile Asp Val
225                 230                 235                 240

Trp Ser Ala Gly Cys Val Leu Ala Glu Leu Leu Leu Gly Gln Pro Ile
                245                 250                 255

Phe Pro Gly Asp Ser Gly Val Asp Gln Leu Val Glu Ile Ile Lys Val
                260                 265                 270

Leu Gly Thr Pro Thr Arg Glu Gln Ile Arg Glu Met Asn Pro Asn Tyr
            275                 280                 285

Thr Glu Phe Lys Phe Pro Gln Ile Lys Ala His Pro Trp Thr Lys Val
        290                 295                 300

Phe Arg Pro Arg Thr Pro Pro Glu Ala Ile Ala Leu Cys Ser Arg Leu
305                 310                 315                 320

Leu Glu Tyr Thr Pro Thr Ala Arg Leu Thr Pro Leu Glu Ala Cys Ala
                325                 330                 335

His Ser Phe Phe Asp Glu Leu Arg Asp Pro Asn Val Lys Leu Pro Asn
                340                 345                 350

Gly Arg Asp Thr Pro Ala Leu Phe Asn Phe Thr Thr Gln Glu Leu Ser
            355                 360                 365

Ser Asn Pro Pro Leu Ala Thr Ile Leu Ile Pro Pro His Ala Arg Ile
        370                 375                 380

Gln Ala Ala Ala Ser Thr Pro Thr Asn Ala Thr Ala Ala Ser Asp Ala
385                 390                 395                 400

Asn Thr Gly Asp Arg Gly Gln Thr Asn Asn Ala Ala Ser Ala Ser Ala
                405                 410                 415

Ser Asn Ser Thr
            420

<210> SEQ ID NO 4
<211> LENGTH: 1263
<212> TYPE: DNA
<213> ORGANISM: Homo sapiens

<400> SEQUENCE: 4
atgtcagggc ggcccagaac cacctccttt gcggagagct gcaagccggt gcagcagcct      60
tcagcttttg gcagcatgaa agttagcaga gacaaggacg gcagcaaggt gacaacagtg     120
gtggcaactc ctgggcaggg tccagacagg ccacaagaag tcagctatac agacactaaa     180
gtgattggaa atggatcatt tggtgtggta tatcaagcca aactttgtga ttcaggagaa     240
ctggtcgcca tcaagaaagt attgcaggac aagagattta agaatcgaga gctccagatc     300
atgagaaagc tagatcactg taacatagtc cgattgcgtt atttcttcta ctccagtggt     360
gagaagaaag atgaggtcta tcttaatctg gtgctggact atgttccgga aacagtatac     420
agagttgcca gacactatag tcgagccaaa cagacgctcc ctgtgattta tgtcaagttg     480
tatatgtatc agctgttccg aagtttagcc tatccaatt cctttggaat ctgccatcgg     540
```

```
gatattaaac cgcagaacct cttgttggat cctgatactg ctgtattaaa actctgtgac    600
tttggaagtg caaagcagct ggtccgagga gaacccaatg tttcgtatat ctgttctcgg    660
tactataggg caccagagtt gatctttgga gccactgatt atacctctag tatagatgta    720
tggtctgctg gctgtgtgtt ggctgagctg ttactaggac aaccaatatt tccaggggat    780
agtggtgtgg atcagttggt agaaataatc aaggtcctgg gaactccaac aagggagcaa    840
atcagagaaa tgaacccaaa ctacacagaa tttaaattcc ctcaaattaa ggcacatcct    900
tggactaagg tcttccgacc ccgaactcca ccggaggcaa ttgcactgtg tagccgtctg    960
ctggagtata caccaactgc ccgactaaca ccactggaag cttgtgcaca ttcatttttt   1020
gatgaattac gggacccaaa tgtcaaacat ccaaatgggc gagacacacc tgcactcttc   1080
aacttcacca ctcaagaact gtcaagtaat ccacctctgg ctaccatcct tattcctcct   1140
catgctcgga ttcaagcagc tgcttcaacc cccacaaatg ccacagcagc gtcagatgct   1200
aatactggag accgtggaca gaccaataat gctgcttctg catcagcttc caactccacc   1260
tga                                                                 1263

<210> SEQ ID NO 5
<211> LENGTH: 118
<212> TYPE: PRT
<213> ORGANISM: Homo sapiens

<400> SEQUENCE: 5

Met Ser Gly Gly Ser Ser Cys Ser Gln Thr Pro Ser Arg Ala Ile Pro
1               5                   10                  15

Ala Thr Arg Arg Val Val Leu Gly Asp Gly Val Gln Leu Pro Pro Gly
            20                  25                  30

Asp Tyr Ser Thr Thr Pro Gly Gly Thr Leu Phe Ser Thr Thr Pro Gly
        35                  40                  45

Gly Thr Arg Ile Ile Tyr Asp Arg Lys Phe Leu Met Glu Cys Arg Asn
    50                  55                  60

Ser Pro Val Thr Lys Thr Pro Pro Arg Asp Leu Pro Thr Ile Pro Gly
65                  70                  75                  80

Val Thr Ser Pro Ser Ser Asp Glu Pro Pro Met Glu Ala Ser Gln Ser
                85                  90                  95

His Leu Arg Asn Ser Pro Glu Asp Lys Arg Ala Gly Gly Glu Glu Ser
            100                 105                 110

Gln Phe Glu Met Asp Ile
        115

<210> SEQ ID NO 6
<211> LENGTH: 357
<212> TYPE: DNA
<213> ORGANISM: Homo sapiens

<400> SEQUENCE: 6
atgtccgggg gcagcagctg cagccagacc ccaagccggg ccatccccgc cactcgccgg     60
gtggtgctcg gcgacggcgt gcagctcccg cccggggact acagcacgac ccccggcggc    120
acgctcttca gcaccacccc gggaggtacc aggatcatct atgaccggaa attcctgatg    180
gagtgtcgga actcacctgt gaccaaaaca ccccccaaggg atctgcccac cattccgggg    240
gtcaccagcc cttccagtga tgagccccc atggaagcca gcagagcca cctgcgcaat     300 agcccagaag ataagcgggc gggcggtgaa gagtcacagt ttgagatgga catttaa       357

<210> SEQ ID NO 7
```

```
<211> LENGTH: 21
<212> TYPE: PRT
<213> ORGANISM: artificial
<220> FEATURE:
<223> OTHER INFORMATION: Fragment of Homo sapiens Eukaryotic translation
      initiation factor 4E-binding protein 1

<400> SEQUENCE: 7

Pro Gly Asp Tyr Ser Thr Thr Pro Gly Gly Thr Leu Phe Ser Thr Thr
1               5                  10                  15

Pro Gly Gly Thr Arg
            20

<210> SEQ ID NO 8
<211> LENGTH: 27
<212> TYPE: PRT
<213> ORGANISM: artificial
<220> FEATURE:
<223> OTHER INFORMATION: Artificial 4E-BP1 PGK3 substrate

<400> SEQUENCE: 8

Cys Asp Asp Pro Gly Asp Tyr Ser Thr Thr Pro Gly Gly Thr Leu Phe
1               5                  10                  15

Ser Thr Thr Pro Gly Gly Thr Arg Asp Tyr Asp
            20                  25

<210> SEQ ID NO 9
<211> LENGTH: 63
<212> TYPE: DNA
<213> ORGANISM: artificial
<220> FEATURE:
<223> OTHER INFORMATION: Nucleic acid encoding fragment of Homo sapiens
      Eukaryotic translation initiation factor 4E-binding protein 1

<400> SEQUENCE: 9
cccggggact acagcacgac ccccggcggc acgctcttca gcaccacccc gggaggtacc    60
agg                                                                 63
```

US 8,323,919 B2

ASSAY METHODS FOR IDENTIFYING GLYCOGEN SYNTHASE KINASE 3 MODULATORS

REFERENCE TO RELATED APPLICATION

This application claims priority from U.S. Provisional Patent Application Ser. No. 61/246,468, filed Sep. 28, 2009, the entire content of which is incorporated herein by reference.

FIELD OF THE INVENTION

Technology described herein relates generally to methods and compositions for glycogen synthase kinase 3 assays. More specifically described are substrates for glycogen synthase kinase 3 enzymes and methods for their use.

BACKGROUND OF THE INVENTION

Enzymes known as glycogen synthase kinase 3 are serine/threonine protein kinases that catalyze the addition of phosphate molecules on certain serine and threonine amino acid residues in target protein substrates within cells. Phosphorylation of such target protein substrates often results in the modification of their specific activities or function. Thus, these enzymes have a role in regulating cellular functions.

Methods and compositions for glycogen synthase kinase 3 assays continue to be required for detection of glycogen synthase 3 kinase, assessment of glycogen synthase 3 kinase activity and identification of modulators of glycogen synthase 3 kinase.

SUMMARY OF THE INVENTION

Glycogen synthase kinase 3 assays are provided according to embodiments which include contacting a sample to be assayed for glycogen synthase kinase 3 with a 4E-BP1 glycogen synthase kinase 3 substrate under conditions which promote specific interaction of the 4E-BP1 glycogen synthase kinase 3 substrate and glycogen synthase kinase 3; and detecting specific interaction of the 4E-BP1 glycogen synthase kinase 3 substrate and glycogen synthase kinase 3.

According to embodiments, the 4E-BP1 glycogen synthase kinase 3 substrate is selected from the group consisting of: a 4E-BP1 glycogen synthase kinase 3 substrate comprising SEQ ID No. 5 and a 4E-BP1 glycogen synthase kinase 3 substrate encoded by the complement of a nucleic acid which hybridizes to SEQ ID No. 6 under highly stringent hybridization conditions.

According to embodiments, the 4E-BP1 glycogen synthase kinase 3 substrate is selected from the group consisting of: SEQ ID No. 7 and a peptide encoded by the complement of a nucleic acid which hybridizes to SEQ ID No. 9 under highly stringent hybridization conditions.

According to embodiments, the 4E-BP1 glycogen synthase kinase 3 substrate comprises SEQ ID No. 8.

According to embodiments, detecting specific interaction of the 4E-BP1 glycogen synthase kinase 3 substrate and glycogen synthase kinase 3 includes detection of phosphorylation of the 4E-BP1 glycogen synthase kinase 3 substrate.

The included 4E-BP1 glycogen synthase kinase 3 substrate can be primed or non-primed.

Isolated 4E-BP1 glycogen synthase kinase 3 substrates are provided herein which include a peptide selected from the group consisting of: SEQ ID No. 7 and a peptide encoded by a nucleic acid which hybridizes to SEQ ID No. 9 under highly stringent hybridization conditions. According to embodiments, isolated 4E-BP1 glycogen synthase kinase 3 substrates are provide which include a detectable label.

According to embodiments, isolated 4E-BP1 glycogen synthase kinase 3 substrates are provide which include a FRET acceptor.

Methods of identifying a GSK3 modulator are provided according to embodiments which include contacting GSK3, a 4E-BP1 glycogen synthase kinase 3 substrate and a test substance under GSK3 reaction conditions which promote specific interaction of GSK3 and the 4E-BP1 glycogen synthase kinase 3 substrate; and detecting changes in specific interaction of the 4E-BP1 glycogen synthase kinase 3 substrate and GSK 3.

Methods of identifying a GSK3 modulator are provided according to embodiments which include contacting GSK3, a 4E-BP1 glycogen synthase kinase 3 substrate and a test substance under GSK3 reaction conditions which promote specific interaction of GSK3 and the 4E-BP1 glycogen synthase kinase 3 substrate; and detecting changes in specific interaction of the 4E-BP1 glycogen synthase kinase 3 substrate and GSK 3, wherein the 4E-BP1 glycogen synthase kinase 3 substrate is selected from the group consisting of: a 4E-BP1 glycogen synthase kinase 3 substrate comprising SEQ ID No. 5 and a 4E-BP1 glycogen synthase kinase 3 substrate encoded by a nucleic acid which hybridizes to SEQ ID No. 6 under highly stringent hybridization conditions.

Methods of identifying a GSK3 modulator are provided according to embodiments which include contacting GSK3, a 4E-BP1 glycogen synthase kinase 3 substrate and a test substance under GSK3 reaction conditions which promote specific interaction of GSK3 and the 4E-BP1 glycogen synthase kinase 3 substrate; and detecting changes in specific interaction of the 4E-BP1 glycogen synthase kinase 3 substrate and GSK 3, wherein the 4E-BP1 glycogen synthase kinase 3 substrate is selected from the group consisting of: SEQ ID No. 7 and a peptide encoded by the complement of a nucleic acid which hybridizes to SEQ ID No. 9 under highly stringent hybridization conditions.

Methods of identifying a GSK3 modulator are provided according to embodiments which include contacting GSK3, a 4E-BP1 glycogen synthase kinase 3 substrate and a test substance under GSK3 reaction conditions which promote specific interaction of GSK3 and the 4E-BP1 glycogen synthase kinase 3 substrate; and detecting changes in specific interaction of the 4E-BP1 glycogen synthase kinase 3 substrate and GSK 3, wherein the 4E-BP1 glycogen synthase kinase 3 substrate comprises SEQ ID No. 8.

Methods of identifying a GSK3 modulator are provided according to embodiments which include contacting GSK3, a 4E-BP1 glycogen synthase kinase 3 substrate and a test substance under GSK3 reaction conditions which promote specific interaction of GSK3 and the 4E-BP1 glycogen synthase kinase 3 substrate; and detecting changes in specific interaction of the 4E-BP1 glycogen synthase kinase 3 substrate and GSK 3, wherein detecting specific interaction of the 4E-BP1 glycogen synthase kinase 3 substrate and glycogen synthase kinase 3 comprises detection of phosphorylation of the 4E-BP1 glycogen synthase kinase 3 substrate.

Methods of identifying a GSK3 modulator are provided according to embodiments which include contacting GSK3, a 4E-BP1 glycogen synthase kinase 3 substrate and a test substance under GSK3 reaction conditions which promote specific interaction of GSK3 and the 4E-BP1 glycogen synthase kinase 3 substrate; and detecting changes in specific interaction of the 4E-BP1 glycogen synthase kinase 3 substrate and GSK 3, wherein the 4E-BP1 glycogen synthase kinase 3 substrate is primed or non-primed.

Commercial packages for use in detection of glycogen synthase kinase 3are provided according to embodiments which include an isolated 4E-BP1 glycogen synthase kinase 3 substrate and a component selected from: a glycogen synthase kinase 3 enzyme, an antibody specific for a glycogen synthase kinase 3 enzyme and an antibody specific for 4E-BP1.

Commercial packages for use in detection of glycogen synthase kinase 3are provided according to embodiments which include an isolated 4E-BP1 glycogen synthase kinase 3 substrate and an antibody specific for 4E-BP1 phosphorylated at an amino acid corresponding to Thr37 and/or Thr46 of the full length 4E-BP1 of SEQ ID No. 5.

Commercial packages for use in detection of glycogen synthase kinase 3 are provided according to embodiments which include an isolated 4E-BP1 glycogen synthase kinase 3 substrate and an antibody specific for 4E-BP1, wherein the isolated 4E-BP1 glycogen synthase kinase 3 substrate comprises a FRET acceptor and the antibody comprises a FRET donor.

Commercial packages for use in detection of glycogen synthase kinase 3 are provided according to embodiments which include an isolated 4E-BP1 glycogen synthase kinase 3 substrate including a detectable label.

Commercial packages for use in detection of glycogen synthase kinase 3 are provided according to embodiments which include an isolated 4E-BP1 glycogen synthase kinase 3 substrate labeled with a FRET acceptor.

DETAILED DESCRIPTION OF THE INVENTION

Figure 1:
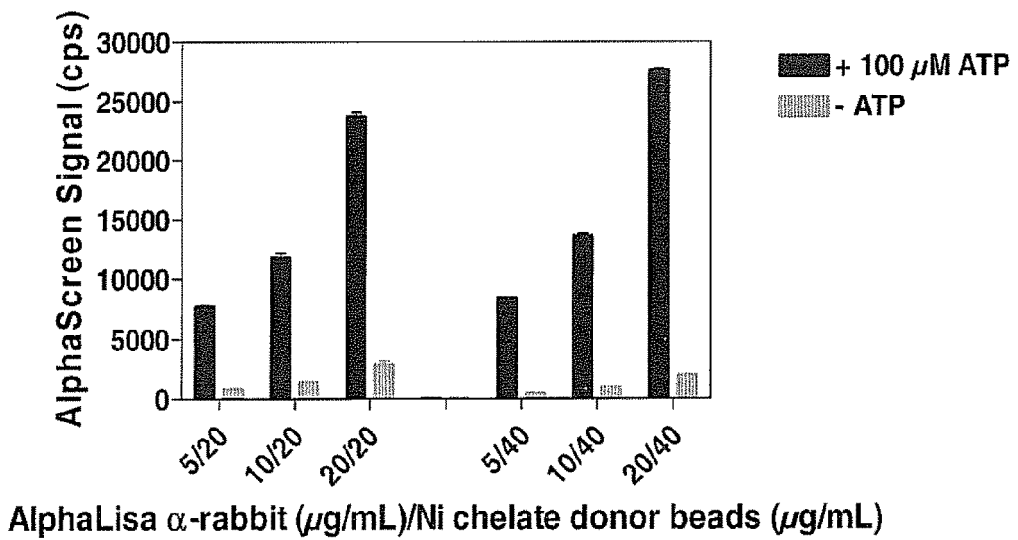
FIG. 1 is a graph showing the results of a glycogen synthase kinase 3-beta (GSK3β) kinase assay using bead-based proximity to detect phosphorylation of full-length eukaryotic translation initiation factor 4E-binding protein 1 (4E-BP1). For this assay, GSK3β was incubated with His-tagged 4E-BP1 in the presence or absence of ATP, then various ratios, 5/20, 10/20, 20/20, 5/40, 10/40, 20/40, shown on the x-axis, of anti-phosphorylated-4E-BP1 antibody (Thr37/46) coupled to the Acceptor beads and nickel chelate-Donor beads are added to form a "molecular sandwich" comprised of [nickel-chelate Donor beads]-[phosphorylated-polyhistidine tagged-4E-BP1 protein]-[rabbit anti-phospho-4E-BP1 immunoglobulin]-[anti-rabbit immunoglobulin-coupled Acceptor beads] if phosphorylation has occurred. Upon irradiation, the proximity of Donor and Acceptor beads in the "molecular sandwich" produce a signal, shown on the y-axis.

Described herein is the discovery of a previously unrecognized interaction between a kinase family and substrate. Specifically, it was found that eukaryotic translation initiation factor 4E-binding protein 1 (4E-BP1, also known as PHAS-I) serves as a substrate for glycogen synthase kinase 3-alpha and beta (GSK3α and GSK3β). Although substrates for GSK3α and GSK3β have been previously described, the phosphorylation of 4E-BP1 by GSK3α and GSK3β was previously unrecognized.

Described herein are the findings that GSK3β phosphorylates 4E-BP1 at positions corresponding to Thr37 and/or Thr46 of human 4E-BP1 (Example 1); that GSK3α and GSK3β phosphorylate the corresponding amino acid residues in a peptide derived from 4E-BP1 (Examples 2 and 3); and that phosphorylation of a 4E-BP1 peptide by GSK3β is inhibited by GSK3β-selective kinase inhibitors (Example 4). Accordingly, provided herein are methods for detecting the activity of GSK3α and/or GSK3β based on the interaction of GSK3α and/or GSK3β and 4E-BP1. Assays described herein have multiple uses, including, but not limited to, study of physiological signaling pathway mediated by GSK3/4E-BP1 interaction and identification of modulators of GSK3/4E-BP1 interaction. Assessment of this interaction can be performed in vitro (for example, in cellular preparations) as well as in vivo (for example, in cells, tissues and organisms).

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; P. Lloyd-Williams et al., Chemical Approaches to the Synthesis of Peptides and Proteins, CRC-Press, 1997; and M. W. Pennington et al., Peptide Synthesis Protocols, Humana Press, 1994; and Herdewijn, P. (Ed.), Oligonucleotide Synthesis: Methods and Applications, Methods in Molecular Biology, Humana Press, 2004.

Assays

Glycogen synthase kinase 3 (GSK3) assays are described herein which include contacting a sample to be assayed for GSK3 with a 4E-BP1 GSK3 substrate under conditions which promote specific interaction of the 4E-BP1 GSK3 substrate and the GSK3. Specific interaction of the 4E-BP1 GSK3 substrate and the GSK3 is then detected.

The term "specific interaction" refers to binding of GSK3 and a 4E-BP1 GSK3 substrate compared to substantially less binding of GSK3 with non-GSK3 substrates. Specific interaction is characterized by selective binding of GSK3 and a 4E-BP1 GSK3 substrate Specific interaction of GSK3 and a 4E-BP1 GSK3 substrate can be detected by, for example, detection of formation of a complex including GSK3 and the 4E-BP1 GSK3 substrate and/or detection of phosphorylation of the 4E-BP1 GSK3 substrate by GSK3.

In mammals, there are two known forms of GSK3: GSK3α and GSK3β. The amino acid sequence of human GSK3α has been reported, for example, as Uniprot accession number P49840 and the amino acid sequence of human GSK3β has been reported, for example, as Uniprot accession number P49841. Amino acid sequences of other GSK3 forms, including GSK3 from non-human species, are publicly available.

An amino acid sequence of human GSK3α is included herein for reference as SEQ ID No. 1. A nucleotide sequence encoding reference human GSK3α, SEQ ID No. 1, is included herein as SEQ ID No. 2.

An amino acid sequence of human GSK3β is included herein for reference as SEQ ID No. 3. A nucleotide sequence encoding reference human GSK3β, SEQ ID No. 3, is included herein as SEQ ID No. 4.

The terms "glycogen synthase kinase 3" and "GSK3" are used interchangeably herein to refer to glycogen synthase kinases 3 alpha and beta having the amino acid sequences set forth in SEQ ID No. 1 and SEQ ID No. 3 respectively, as well as GSK3 variants and GSK3 fragments capable of specifically interacting with eukaryotic translation initiation factor 4E-binding protein 1.

The term "GSK3 variants" refers to GSK3 having at least 70%, 75%, 80%, 85%, 90%, 91%, 92%, 93%, 94%, 95%, 96%, 97%, 98%, 99%, or 100% identity to SEQ ID No. 1 and/or SEQ ID No. 3.

The terms "glycogen synthase kinase 3" and "GSK3" encompass GSK3 encoded by the complement of a nucleic acid sequence that hybridizes under high stringency hybridization conditions to SEQ ID No. 2 and/or SEQ ID No. 4.

Eukaryotic translation initiation factor 4E-binding protein 1 (4E-BP1) is a component of the protein complex 'eukaryotic translation initiation factor 4F,' which has been characterized as involved in aspects of the protein translation process. An amino acid sequence of human 4E-BP1 is included herein for reference as SEQ ID No. 5. A nucleotide sequence encoding reference human 4E-BP1, SEQ ID No. 5, is included herein as SEQ ID No. 6.

The terms "eukaryotic translation initiation factor 4E-binding protein 1 substrate for glycogen synthase kinase 3" and "4E-BP1 GSK3 substrate" are used interchangeably herein to refer to eukaryotic translation initiation factor 4E-binding protein 1 having the amino acid sequence set forth in SEQ ID No. 5, variants and fragments thereof capable of being specifically phosphorylated by glycogen synthase kinase 3.

The term "variants" refers to 4E-BP1 GSK3 substrates having at least 70%, 75%, 80%, 85%, 90%, 91%, 92%, 93%, 94%, 95%, 96%, 97%, 98%, 99%, or 100% identity to the 4E-BP1 protein having the amino acid sequence set forth in SEQ ID No. 5 wherein the amino acid sequence includes at least one GSK3 phosphorylation motif. The term "GSK3 phosphorylation motif" refers to the amino acid sequence Thr-X-X-X-Thr, where each X is an independently selected amino acid.

The terms "eukaryotic translation initiation factor 4E-binding protein 1 substrate for glycogen synthase kinase 3" and "4E-BP1 GSK3 substrate" encompass GSK3 substrates encoded by the complement of a nucleic acid sequence that hybridizes under high stringency hybridization conditions to SEQ ID No. 6, where the encoded 4E-BP1 GSK3 substrate includes at least one GSK3 phosphorylation motif.

The terms "eukaryotic translation initiation factor 4E-binding protein 1 substrate for glycogen synthase kinase 3" and "4E-BP1 GSK3 substrate" encompass fragments of at least 10 amino acids which have 70%, 75%, 80%, 85%, 90%, 91%, 92%, 93%, 94%, 95%, 96%, 97%, 98%, 99%, or 100% identity to SEQ ID No. 7, wherein the fragment includes at least one phosphorylation motif Thr-X-X-X-Thr, where each X is an independently selected amino acid.

According to embodiments, a 4E-BP1 GSK3 substrate includes the amino acid sequence PGDYSTTPGGTLFST-TPGGTR (SEQ ID No. 7). According to embodiments, a 4E-BP1 GSK3 substrate is encoded by the complement of a nucleic acid sequence that hybridizes under high stringency hybridization conditions to SEQ ID No. 9 where the encoded GSK3 substrate includes at least one GSK3 phosphorylation motif.

As used herein, the terms "variant" and "variants" refer to naturally occurring genetic mutants and recombinantly prepared variation of a protein or peptide compared to a reference protein or peptide. For example, variants of a specified protein or peptide are those containing mutations where one or more amino acid residues have been modified by amino acid substitution, addition, or deletion. Such mutations can be introduced using standard recombinant molecular biology techniques, such as site-directed mutagenesis and PCR-mediated mutagenesis. One of skill in the art will recognize that one or more amino acid mutations can be introduced without altering the functional properties of a given protein or peptide.

The terms "fragment" and "polypeptide portion" are used interchangeably herein to refer to a polypeptide or peptide which is part of, but smaller than, a reference full length peptide or polypeptide.

According to embodiments, proteins and protein fragments included in methods, compositions and/or commercial packages are human proteins and fragments of human proteins. Orthologs of human proteins and protein fragments can be used from any of various species, including, without limitation, organisms including mammals, birds, reptiles, amphibians, insects, plants, microorganisms and eukaryotic microorganisms such as yeast.

Conservative amino acid substitutions can be made in a protein or peptide to produce variants. Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, glycine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, praline, threonine, serine, valine, all typically considered to be small.

The terms "polypeptide," "peptide" and "protein" refer to a chain of amino acids linked by peptide bonds. These terms encompass oligopeptides having from 2—about 10 peptide bond linked amino acids and polypeptides having about 10 or more peptide bond linked amino acids.

The terms "amino acid" and "amino acid residue" are well-known in the art. In general the abbreviations used herein for designating the amino acids and protective groups conform to those used by the IUPAC-IUB Commission on Biochemical Nomenclature, see for example Biochemistry (1972) 11:1726-1732. The following abbreviations are commonly used to refer to specific amino acids and/or amino acid residues: A or Ala for alanine, C or Cys for cysteine, D or Asp for aspartic acid, E or Glu for glutamic acid, F or Phe for phenylalanine, G or Gly for glycine, H or His for histidine, I or Ile for isoleucine, K or Lys for lysine, L or Leu for leucine, M or Met for methionine, N or Asn for asparagine, P or Pro for proline, Q or Gln for glutamine, R or Arg for arginine, S or Ser for serine, T or Thr for threonine, V or Val for valine, W or Trp for tryptophan, and Y or Tyr for tyrosine. The term "amino acid residue" further includes analogs, derivatives and congeners of amino acids, as well as C-terminal or N-terminal protected amino acid derivatives. For example, an amino acid analog may be used wherein a side chain is modified while still providing a carboxyl, amino or other reactive functional group. For example, amino acid analogs illustratively include canavanine, cyanoalanine, diaminobutyric acid, diaminopimelic acid, dihydroxy-phenylalanine norleucine, 3-phosphoserine, homoserine, 5-hydroxytryptophan, 1-methylhistidine, 3-methylhistidine, and ornithine. Well-known modified amino acids and cyclic amino acids can be included in embodiments of tyrosine kinase substrate peptides.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions X100%). In one embodiment, the two sequences are the same length.

The determination of percent identity between two sequences can also be accomplished using a mathematical algorithm. A preferred, non limiting example of a mathematical algorithm utilized for the comparison of two sequences is the algorithm of Karlin and Altschul, 1990, PNAS 87:2264 2268, modified as in Karlin and Altschul, 1993, PNAS. 90:5873 5877. Such an algorithm is incorporated into the NBLAST and XBLAST programs of Altschul et al., 1990, J. Mol. Biol. 215:403. BLAST nucleotide searches are performed with the NBLAST nucleotide program parameters set, e.g., for score=100, wordlength=12 to obtain nucleotide sequences homologous to a nucleic acid molecules of the present invention. BLAST protein searches are performed with the XBLAST program parameters set, e.g., to score 50, wordlength=3 to obtain amino acid sequences homologous to a protein molecule of the present invention. To obtain gapped alignments for comparison purposes, Gapped BLAST are utilized as described in Altschul et al., 1997, Nucleic Acids Res. 25:3389 3402. Alternatively, PSI BLAST is used to perform an iterated search which detects distant relationships between molecules (Id.). When utilizing BLAST, Gapped BLAST, and PSI Blast programs, the default parameters of the respective programs (e.g., of XBLAST and NBLAST) are used (see, e.g., the NCBI website). Another preferred, non limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps. In calculating percent identity, typically only exact matches are counted.

It is appreciated that due to the degenerate nature of the genetic code, alternate nucleic acid sequences encode proteins and peptides described herein and variants thereof, and that such alternate nucleic acids may be used.

The term "complementary" refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100% complementary to a region of the nucleotide sequence 5'-TTAGCTGG-3'.

The terms "hybridization" and "hybridizes" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and F. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

High stringency conditions generally include low ionic strength and high temperature for washing.

A non-limiting example of high stringency hybridization conditions is hybridization of nucleic acids over about 100 nucleotides in length in a solution containing 6×SSC, 5× Denhardt's solution, 30% formamide, and 100 micrograms/ml denatured salmon sperm at 37° C. overnight followed by washing in a solution of 0.1×SSC and 0.1% SDS at 60° C. for 15 minutes. SSC is 0.15M NaCl/0.015M Na citrate. Denhardt's solution is 0.02% bovine serum albumin/0.02% FICOLL/0.02% polyvinylpyrrolidone.

A further non-limiting example of high stringency hybridization conditions is hybridization of nucleic acids over about 50 nucleotides in length in a solution containing 1×SSC, 50% formamide, at 42° C. followed by washing in a solution of 0.3×SSC at 65° C.

Moderately stringent conditions for nucleic acids over 50 nucleotides in length are exemplified by hybridization in a solution containing 6×SSC, 50% formamide, at 40° C. followed by washing in a solution of 2×SSC at 50° C.

The term "nucleic acid" as used herein refers to RNA or DNA molecules having more than one nucleotide in any form including single-stranded, double-stranded, oligonucleotide or polynucleotide.

The term "isolated" as used herein refers to a substance that has been separated from contaminating materials not intended to be associated with the substance and that would interfere with use of the substance in assays or other uses. The term isolated used herein also refers to non-naturally occurring nucleic acids and proteins, such as fusion proteins or modified proteins according to embodiments of the present invention and nucleic acids encoding the fusion proteins or modified proteins since such non-naturally occurring nucleic acids and proteins are not found in nature. An "isolated" material may be, but is not necessarily, pure. Generally, an isolated substance described herein is at least about 80% pure, at least about 90% pure, at least about 95% pure, or greater than about 99% pure. Purification is achieved using well-known standard methodology such as fractionation and/or chromatography, such as ammonium sulfate precipitation and elution chromatography such as size exclusion chromatography, displacement chromatography, ion exchange chromatography and bioaffinity chromatography. Exemplary purification methodology relating to peptides and proteins is described in S. Doonan, Protein Purification Protocols Humana Press, 1996.

The terms "isolated" with reference to peptides describes peptides which are substantially free of material such as chemical precursors or other chemicals used in peptide synthesis or substantially free of cellular material such as contaminating polypeptides when produced recombinantly.

In an embodiment, a method for detecting GSK3α and/or GSK3β and/or detecting GSK3 enzymatic activity involves contacting GSK3α and/or GSK3β with 4E-BP1 under conditions that promote specific interaction of GSK3 and 4E-BP1, and detecting the specific interaction between GSK3α and/or GSK3β with 4E-BP1. Detecting of this specific interaction can be, for example, by protein-protein interaction detection methods, kinase activity detection methods, phosphorylation detection methods and combinations thereof.

Assays according to embodiments are kinase assays. Particular read-outs for detection of specific interaction of GSK3 and 4E-BP1 GSK substrate are phosphorylation of 4E-BP1 by GSK3α and phosphorylation of 4E-BP1 by GSK3β.

For example, detecting the activity of GSK3α and/or GSK3β can involve detecting the presence of a phosphorylated 4E-BP1. The method can be performed in a direct or indirect assay format. Kinase assays in particular formats, such as assay of radioactive phosphate incorporation, can be performed with unlabeled 4E-BP1 substrates. Most non-radioactive kinase assays, such as TR-FRET, require that the 4E-BP1 substrate be detectably labeled. Therefore, 4E-BP1 GSK3 substrates can be used in unlabeled and labeled form, depending on the selected assay format.

According to embodiments, a 4E-BP1 GSK3 substrate is labeled for use in an assay to detect GSK3 and/or to detect GSK3 kinase activity. A 4E-BP1 GSK3 substrate can be labeled using any detectable label.

The term "detectable label" refers to a substance that can be measured and/or observed, visually or by any appropriate method illustratively including radiometric, spectroscopic, optical, photochemical, biochemical, enzymatic, electrical and/or immunochemical methods of detection, to indicate presence of the label. Non-limiting examples of non-radioactive detectable labels that can be used in conjunction with compositions and methods described herein illustratively include a fluorescent moiety, a chemiluminescent moiety, a bioluminescent moiety, a magnetic particle, a member of a specific binding pair, and a chromophore.

For example, a 4E-BP1 GSK3 substrate can be labeled with a dye, such as a fluorophore, a chromophore, or a member of a specific binding pair such as biotin. The term "member of a specific binding pair" refers to a substance that specifically recognizes and interacts with a second substance exemplified by specific binding pairs such as biotin-avidin, biotin-streptavidin, antibody-antigen, and target-aptamer.

Non-limiting examples of detectable labels that can be used include fluorescent dyes such as fluorescein, fluorescein isothiocyanate, rhodamine, rhodamine isothiocyanate, Texas Red, cyanine dyes such as Cyanine 3 and Cyanine 5, and ALEXA dyes; chromophores such as horseradish peroxidase, alkaline phosphatase and digoxigenin; binding partners such as biotin and biotin derivatives.

4E-BP1 GSK3 substrates according to embodiments include a FRET acceptor as a detectable label. FRET is a process involving transfer of energy by a donor label to an acceptor label when the donor label and acceptor label are in proximity.

In embodiments of the present invention, 4E-BP1 GSK3 substrates are coupled to a fluorescence resonance energy transfer (FRET) donor or acceptor. In further embodiments, substrate peptides are coupled to a FRET acceptor.

Detectable labels operable in FRET techniques of the present invention include flurophores and luminescent compounds illustratively including those described in Haughland, R. P., The Handbook, A Guide to Fluorescent Probes and Labeling Technologies, 10th Ed., 2005; Lakowicz, J. R., Principles of Fluorescence Spectroscopy, Springer, 3rd ed., 2006; 4-acetamido-4'-isothiocyanatostilbene-2,2'disulfonic acid; acridine and derivatives such as acridine and acridine isothiocyanate; 4-amino-N-[3-vinylsulfonyl)phenyl]naphthalimide-3,5 disulfonate, Lucifer Yellow VS; N-(4-anilino-1-naphthyl)maleimide; anthranilamide, Brilliant Yellow; BIODIPY fluorophores (4,4-difluoro-4-bora-3a,4a-diaza-s-indacenes); coumarin and derivatives such as coumarin, 7-amino-4-methylcoumarin (AMC, Coumarin 120), 7-amino-4-trifluoromethylcouluarin (Coumaran 151); cyanosine; DAPDXYL sulfonyl chloride; 4',6-diaminidino-2-phenylindole (DAPI); 5',5''-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylaminolnaphthalene-1-sulfonyl chloride (DNS, dansyl chloride); 4-4'-dimethylaminophenylazo)benzoic acid (DABCYL); 4-dimethylaminophenylazophenyl-4'-isothiocyanate (DABITC); EDANS (5-[(2-aminoethyl)amino]naphthalene-1-sulfonic acid), eosin and derivatives such as eosin isothiocyanate; erythrosin and derivatives such as erythrosin B and erythrosin isothiocyanate; ethidium such as ethidium bromide; fluorescein and derivatives such as 5-carboxyfluorescein (FAM), 5-(4,6-dichlorotriazin-2-yl) aminofluorescein (DTAF), 2',7'-dimethoxy-4',5'-dichloro-6-carboxyfluorescein (JOE) and fluorescein isothiocyanate (FITC); fluorescamine; green fluorescent protein and derivatives such as EBFP, EBFP2, ECFP, and YFP; IAEDANS (5-({2-[(iodoacetyl)amino]ethyl}amino)naphthalene-1-sulfonic acid), Malachite Green isothiocyanate; 4-methylumbelliferone; orthocresolphthalein; nitrotyrosine; pararosaniline; Phenol Red; B-phycoerytnin; o-phthaldialdehyde; pyrene and derivatives such as pyrene butyrate, 1-pyrenesulfonyl chloride and succinimidyl 1-pyrene butyrate; QSY 7; QSY 9; Reactive Red 4 (Cibacron® Brilliant Red 3B-A); rhodamine and derivatives such as 6-carboxy-X-rhodamine (ROX), G-carboxyrhodamine (Rhodamine 6G), rhodamine isothiocyanate, lissamine rhodamine B sulfonyl chloride, rhodamine B, rhodamine 123, sulforhodamine B, sulforhodamine 101 and sulfonyl chloride derivative of sulforhodamine 101 (Texas Red); N,N,N',N-tetramethyl-carboxyrhodamine (TAMRA); tetramethyl rhodamine; tetramethyl rhodamine isothiocyanate (TRITC); riboflavin; rosolic acid and terbium chelate derivatives.

Examples of FRET donor/acceptor fluorophore pairs are described in Lakowicz, J. R., Principles of Fluorescence Spectroscopy, Springer, 3rd ed., 2006; and Haughland, R. P., The Handbook, A Guide to Fluorescent Probes and Labeling Technologies, 10th Ed., 2005.

One of skill in the art can easily determine which of various fluorophores are to be used as FRET donor/acceptor fluorophore pairs in a particular application. Examples of FRET acceptors include, but are not limited to, tetramethylrhodamine, fluorescein, 4-(4'-dimethylaminophenylazo)benzoic acid (dabcyl), BODIPY FL, QSY 7, QSY 9, Cy5 and Alexa647.

In particular embodiments, 4E-BP1 GSK3 substrates are labeled with ULIGHT FRET acceptor.

Labeling of 4E-BP1 GSK3 substrates described herein can be achieved by any of various methods known to the skilled artisan. For example, the NH2-terminus of the peptide can be labeled directly with a molecule having a NHS ester reactive group.

A detectable label can be conjugated to 4E-BP1 GSK3 substrates directly or indirectly, such as through a linker. Broadly described, conjugation of the detectable label to 4E-BP1 GSK3 substrates includes reaction of a functional group of the detectable label or linker that selectively reacts with a peptide functional group such as a terminal amino group, a terminal carboxyl group or a functional group of an amino acid side chain.

Non-limiting examples of functional groups which react with sulfhydryl groups of cysteine-containing peptides include epoxide, haloacetyl, and maleimide. Non-limiting examples of functional groups which react with amino groups include N-hydroxysuccinimidyl esters, carbodiimides, aldehydes, ketones, glyoxals, imidoesters, isothiocyanates, sulfonyl chlorides and acyl azides. Non-limiting examples of functional groups which react with carboxylic acid groups include amines, hydrazides, carbodiimides, diazoalkanes, diazoacetyls and carbon yldiimidazole. Additional functional groups and exemplary conjugation reactions are known in the art as exemplified in G. T. Hermanson, Bioconjugate Techniques, 2nd Edition, Academic Press, 2008.

A detectable label can be incorporated during and/or after 4E-BP1 GSK3 substrate synthesis. A detectable label can be inserted at any position in a 4E-BP1 GSK3 substrate where it does not interfere with the recognition of the 4E-BP1 GSK3 substrate by the GSK3 being assayed, or with the detection of the phospho-threonine residues in antibody-based assays.

In particular embodiments, 4E-BP1 GSK3 substrates are labeled by reaction of a cysteine residue of the 4E-BP1 GSK3 substrates with a fluorescent dye or linker having a functional group, such as a maleimide group, that reacts with a cysteine to create a covalent link between the dye and the 4E-BP1 GSK3 substrate. In such embodiments, at least one cysteine residue is included in the 4E-BP1 GSK3 substrate and may be positioned anywhere in the 4E-BP1 GSK3 substrate, such as at the N-terminus of the 4E-BP1 GSK3 substrate or at the C-terminus of the 4E-BP1 GSK3 substrate.

As will be recognized by one of skill in the art, the 4E-BP1 GSK3 substrates may include either a free ($NH_2$) or acylated amine and the C-terminus may include free acid (COOH) or amidated ($CONH_2$) terminus. Additional or alternative modifications may be made, for instance, to facilitate peptide labeling.

A 4E-BP1 GSK3 substrate can be primed or non-primed. As used herein, the term "primed" means that one or more serine and/or threonine amino acid residues of a 4E-BP1 GSK3 substrate phosphorylation motif are phosphorylated prior to use as GSK3 substrate in an assay provided herein. Up until the present description, all known reported GSK3 enzyme assays using peptide substrates have used a primed in the motif SIT XXX pS/pT, where the first serine or threonine is phosphorylated by GSK3 enzymes only when the residue located at a distance of 4 amino acid residues has been pre-phosphorylated (generally by some other kinase, usually called priming kinase). Exemplary known primed GSK3 peptide substrates include glycogen synthase (GS)-derived peptide, which was pre-phosphorylated at serine 657, with GSK3 phosphorylation sites at serine 653, serine 649, serine 645 and serine 641; insulin receptor substrate-1 (IRS-1)-derived peptide, which was pre-phosphorylated at serine 336, with GSK3 phosphorylation sites at serine 332 and serine 236; and CREB-derived peptide (CREBtide), which was pre-phosphorylated at serine 133, with a GSK3 phosphorylation site at serine 129.

In an embodiment, provided herein is a 4E-BP1 GSK3 substrate that is non-primed as well as assays including a non-primed 4E-BP1 GSK3 substrate and commercial packages including a non-primed 4E-BP1 GSK3 substrate. In a particular embodiment, a 4E-BP1 GSK3 substrate is provided which includes non-primed SEQ ID No. 5, SEQ ID No. 7 or SEQ ID No. 8, or another 4E-BP1 GSK3 substrate that has 4E-BP1 GSK3 substrate activity, wherein the 4E-BP1 GSK3 substrate is non-primed.

In an embodiment, provided herein is a 4E-BP1 GSK3 substrate that is primed as well as assays including a primed 4E-BP1 GSK3 substrate and commercial packages including a primed 4E-BP1 GSK3 substrate. In a particular embodiment, a 4E-BP1 GSK3 substrate is provided which includes primed SEQ ID No. 5, SEQ ID No. 7 or SEQ ID No. 8, or another 4E-BP1 GSK3 substrate that has 4E-BP1 GSK3 substrate activity, wherein the 4E-BP1 GSK3 substrate is primed.

Any appropriate method, illustratively including radiometric, spectroscopic, optical, photochemical, biochemical, enzymatic, electrical and/or immunochemical is used to detect a signal of a detectable label in an assay described herein.

The 4E-BP1 GSK3 substrates can be generated using well-known chemical methods of direct peptide synthesis, such as manual or automated solid-phase peptide synthesis, for example as described in P. Lloyd-Williams et al., Chemical Approaches to the Synthesis of Peptides and Proteins, CRC-Press, 1997; and M. W. Pennington et al., Peptide Synthesis Protocols, Humana Press, 1994. In addition, tyrosine kinase substrate peptides can be generated using well-known recombinant methodology for producing peptides, for example J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; and Herdewijn, P. (Ed.), Oligonucleotide Synthesis: Methods and Applications, Methods in Molecular Biology, Humana Press, 2004.

Proteins and peptides included in methods, compositions and/or commercial packages described herein can be made using recombinant methodology using well-known techniques of molecular biology, for example, as described in standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; and Herdewijn, P. (Ed.), Oligonucleotide Synthesis: Methods and Applications, Methods in Molecular Biology, Humana Press, 2004.

For example, an expression cassette which includes a nucleic acid sequence encoding an a desired protein is expressed to produce the encoded protein. The nucleic acid sequence encoding the desired protein is operably linked to one or more regulatory nucleic acid sequences which facilitates expression of the nucleic acid sequence in an appropriate host cell and/or in a cell-free expression system.

An expression cassette can be incorporated into a vector, such as an expression vector and/or cloning vector. The term "vector" refers to a recombinant nucleic acid vehicle for transfer of a nucleic acid. Exemplary vectors are plasmids, cosmids, viruses and bacteriophages. Particular vectors are known in the art and one of skill in the art will recognize an appropriate vector for a specific purpose.

A host cell for expression of given protein or peptide can be prokaryotic or eukaryotic, such as bacterial, plant, insect, fungus, yeast, and mammalian cells.

The term "operably linked" refers to a nucleic acid in functional relationship with a second nucleic acid. Included regulatory nucleic acid sequences illustratively include a promoter, an enhancer, a DNA and/or RNA polymerase binding site, a ribosomal binding site, a polyadenylation signal, a transcription start site, a transcription termination site or an internal ribosome entry site (IRES).

An expression cassette can also encode a polyhistidine tag peptide to facilitate purification of the expressed fusion protein, a detectable label and/or a selection marker.

An expression vector is introduced into a host cell using well-known techniques such as infection or transfection, including calcium phosphate transfection, liposome-mediated transfection, electroporation and sonoporation. Expression constructs and methods for their generation and use to express a desired protein are known in the art, as described, for example, in Sambrook et al., Molecular Cloning: A Laboratory Manual, Cold Spring Harbor Laboratory Press, 2001; Ausubel, F. et al., (Eds.), Protocols in Molecular Biology, Wiley, 2002; and S. J. Higgins and B. D. Hames (Eds.), Protein Expression: A Practical Approach, Oxford University Press, USA, 1999.

GSK3 assays according to embodiments include contacting a sample to be assayed for GSK3 activity with a GSK3 substrate composition as described herein and detecting specific interaction of GSK3 and a 4E-BP1 GSK3 substrate, such as, but not limited to, by detection of phosphorylation of the 4E-BP1 GSK3 substrate. The sample can be a biological sample obtained from a subject or can be obtained from in vitro cell or tissue sources, including, but not limited to, cultured primary cells or cell lines. A sample obtained from a subject can be any biological material containing or suspected of containing GSK3, including, but not limited to, blood or a blood fraction, serum, plasma, urine, saliva, mucosal secretions, tears, milk, semen and tissue extracts.

A subject can be a human or any animal such as, but not limited to, non-human primates and non-primates such as cows, horses, pigs, sheep, goats, rodents, cats, dogs and birds.

A sample can be isolated GSK3, such as isolated GSK3 produced by recombinant methodology or GSK3 isolated from a biological sample.

Any GSK3 assay format can be used in conjunction with assays described herein, including, but not limited to, immunoblotting, gel electrophoresis of labeled substrates, filter binding, immunoprecipitation, scintillation proximity assay, time-resolved fluorescence resonance energy transfer (TR-FRET), and fluorescence polarization assays.

Assays of the present invention are performed under conditions which promote specific interaction of GSK3 and a 4E-BP1 GSK3 substrate, such as GSK3 reaction conditions.

The term "GSK3 reaction conditions" refers to chemical reaction conditions in which GSK3 phosphorylates a GSK3 phosphorylation substrate. GSK3 reaction conditions according to the present invention include GSK3 and a GSK3 substrate. An assay according to embodiments of the present invention can be performed in cells or under cell-free conditions. Additional aspects of GSK3 reaction conditions include, for example, suitable reaction temperature, pH and identity of reaction medium where present, all of which are known in the art.

Assays described can be performed in any suitable container. In particular embodiments, for example, where multiple samples are to be assayed, a multi-chamber container can be used. Multi-chamber containers illustratively include multi-depression substrates such as slides, silicon chips or trays. In some embodiments, each sample is disposed in a different well of a multi-well plate. For example, a multi-well plate can be a 96-well, 384-well, 1024-well or 1536-well assay plate.

Examples described herein include chemiluminescence (AlphaLISA technology) and fluorescence-based proximity assays useful for detecting the activity of GSK3α and/or GSK3β based on phosphorylation of 4E-BP1 GSK3 substrate.

Assays to Identify Modulators

Provided are methods for identifying compounds that alter the interaction between GSK3α and 4E-BP1, and GSK3β and 4E-BP1.

In an embodiment, a method for identifying compounds that alter the interaction between GSK3α and/or GSK3β and 4E-BP1 polypeptide involves contacting GSK3α and/or GSK3β and the 4E-BP1 polypeptide, or a portion thereof, under conditions that allow GSK3α and/or GSK3β kinase activity to phosphorylate 4E-BP1 polypeptide, or portion thereof; detecting the interaction between GSK3α and/or GSK3β and 4E-BP1 polypeptide, or portion thereof, in the presence and absence of a candidate compound; and determining whether presence of the candidate compound results in an alteration of the interaction between GSK3α and/or GSK3β and 4E-BP1. The alteration can be an increase or decrease in interaction between GSK3α and/or GSK3β and 4E-BP1.

In an embodiment, a method for identifying compounds that alter the interaction between GSK3α and/or GSK3β and 4E-BP1 polypeptide involves detecting 4E-BP1 phosphorylation. The method involves contacting GSK3α and/or GSK3β and the 4E-BP1 polypeptide, or a portion thereof, under conditions that allow GSK3α and/or GSK3β kinase activity to phosphorylate 4E-BP1 polypeptide, or portion thereof; detecting the phosphorylation of the 4E-BP1 polypeptide, or portion thereof, in the presence and absence of a candidate compound; and determining whether presence of the candidate compound alters GSK3α and/or GSK3β kinase activity. The alteration can be an increase or decrease in phosphorylation of the 4E-BP1 polypeptide, or a portion thereof.

The above methods can be used, for example, for determining whether a candidate compound is capable of functioning as an activator or inhibitor of interaction between GSK3α and/or GSK3β and 4E-BP1 polypeptide; as an activator or inhibitor of phosphorylation of 4E-BP1 polypeptide or portion thereof by GSK3α and/or GSK3β; and for determining whether a candidate compound is capable of functioning as an activator or inhibitor of GSK3α and/or GSK3β kinase generally.

Methods of identifying a modulator of GSK3 are provided which include contacting GSK3 and a 4E-BP1 GSK3 substrate in the presence of a test substance. Phosphorylation of the 4E-BP1 GSK3 substrate detected in the presence and absence of the test substance is compared, thereby identifying an increase or decrease in phosphorylation in the presence of the test substance.

The term "test substance" refers to any substance, naturally occurring or synthetic, to be tested for the capacity to directly or indirectly modulate the activity of GSK3 to phosphorylate a 4E-BP1 GSK3 substrate relative to a control. A "test substance" can be a synthetic or naturally occurring compound, a small organic or inorganic molecule, a protein, a peptide, a nucleic acid, a carbohydrate, a polysaccharide or a combination of any of these.

A test substance can be a complex mixture of molecules, such as a cell extract. A test substance can be in the form of a mixture of compounds, exemplified by a library of compounds, such as a combinatorial or randomized library. A library of test substances such as a spatially addressable solid phase libraries and solution phase libraries can be used.

The term "modulator" refers to molecules that are identified using an assay according to embodiments of the present invention that increases, decreases, facilitates, sensitizes or otherwise affects the activity of GSK3 to phosphorylate a 4E-BP1 GSK3 substrate relative to a control.

Substrates

Further provided are 4E-BP1 peptide compositions for detecting the activity of GSK3α and/or GSK3β.

As is described herein, the phosphorylation of 4E-BP1 by GSK3α and GSK3β has been discovered. As such, it is desirable to assay the interaction between these newly recognized binding partners, such as by a phosphorylation assay. A phosphorylation assay can be performed by incubating a selected GSK3 with 4E-BP1, using any of a variety of well-known assay formats. Oftentimes it is desirable to use a peptide portion of 4E-BP1 as a substrate in phosphorylation assays because peptide substrates are generally less expensive to prepare, easy to chemically alter (for example, by labeling), and have greater stability in comparison to full-length proteins.

Thus, provided herein are 4E-BP1 peptides useful as GSK3 substrates for detecting the activities of GSK3α and/or GSK3β.

For example, provided is a 4E-BP1 GSK3 substrate peptide having the amino acid sequence PGDYSTTPGGTLFST-TPGGTR (SEQ ID No. 7).

If desired, one or more amino acids of SEQ ID No. 7 can be substituted with another amino acid or amino acid modification so long as the resultant peptide retains 4E-BP1 GSK3 substrate activity. The peptide also can have one or more amino acids removed or added to the N- and/or C-terminus, so long as the resultant peptide retains 4E-BP1 GSK3 substrate activity. For example, a longer peptide encompassing SEQ ID No. 7 can be prepared based on extending the natural amino acid sequence of 4E-BP1 (such as human 4E-BP1: SEQ ID No. 5) on either or both the N- and C-terminus of SEQ ID No. 7.

The 4E-BP1 GSK3 substrate of SEQ ID No. 7 can be modified such that the 4E-BP1 GSK3 substrate includes only one of the two GSK3 phosphorylation motifs.

Alternatively, or in addition, functional amino acids and sequences can be added to either of both the N- and C-terminus of SEQ ID No. 7. Functional amino acids and amino acid sequences can include, for example, a capture tag, a detectable label, an amino acid sequence that alters solubility, an amino acid sequence with another phosphorylation site for GSK3 or different kinase activity.

A 4E-BP1 GSK3 substrate can be primed or non-primed. In a particular embodiment, the 4E-BP1 GSK3 substrate peptide includes primed or non-primed SEQ ID No. 7.

Additionally, if desired, the 4E-BP1 GSK3 substrate peptide can be modified to contain a detectable tag, such as by incorporating a labeled amino acid modification or labeling the peptide with a detectable moiety. As described herein, exemplary detectable labels include moieties capable of producing fluorescence, luminescence, or other detectable property, as well as moieties capable of being captured or bound by a binding partner. Methods for labeling peptides are well known. Particular chemistries can be selected based on the amino acid to be labeled.

A specific example of a 4E-BP1 peptide useful for the methods described herein, which is exemplified below, is a 4E-BP1 peptide labeled at the N-terminal cysteine with a ULight fluorescent moiety.

For example, provided is a 4E-BP1 peptide having the amino acid sequence CDDPGDYSTTPGGTLFSTTPG-GTRDYD (SEQ ID No. 8). It has been found that GSK3α and GSK3β can phosphorylate this peptide at amino acid residues corresponding to Thr37 and/or Thr46 of the full-length 4E-BP1 polypeptide.

If desired, one or more amino acids of SEQ ID No. 8 can be substituted with another amino acid or amino acid modification so long as the resultant peptide retains 4E-BP1 substrate activity. The peptide also can have one or more amino acids removed or added to the N- and/or C-terminus, so long as the resultant peptide retains 4E-BP1 substrate activity. For example, a longer peptide encompassing SEQ ID No. 8 can be prepared based on extending the natural amino acid sequence of 4E-BP1 on either or both the N- and C-terminus of SEQ ID No. 8. Alternatively, or in addition, functional amino acids and sequences can be added to either of both the N- and C-terminus of SEQ ID No. 8.

The 4E-BP1 GSK3 substrate of SEQ ID No. 8 can be modified such that the 4E-BP1 GSK3 substrate includes only one of the two GSK3 phosphorylation motifs.

In a particular embodiment, the 4E-BP1 GSK3 substrate peptide includes primed or non-primed SEQ ID No. 8, or another primed or non-primed 4E-BP1 GSK3 substrate peptide that has 4E-BP1 substrate activity.

Commercial Packages

Commercial packages useful for detecting activity of GSK3α and/or GSK3β are additionally provided.

Provided herein are commercial packages useful for carrying out methods described herein. The commercial packages can be used, for example, to detect the interaction between GSK3α and/or GSK3β and 4E-BP1 or a portion thereof, and to detect the kinase activity of GSK3α and/or GSK3β based on phosphorylation of the 4E-BP-1 polypeptide or a portion thereof.

Embodiments of commercial packages include a 4E-BP1 GSK3 substrate and a component selected from: a glycogen synthase kinase 3 enzyme, an antibody specific for a glycogen synthase kinase 3 enzyme an antibody specific for GSK3 phosphorylated 4E-BP1 GSK3 substrate, an antibody specific for non-phosphorylated 4E-BP1 GSK3 substrate and a combination of any of these.

Embodiments of commercial packages include a 4E-BP1 GSK3 substrate selected from: a 4E-BP1 GSK3 substrate including the amino acid sequence of SEQ ID No. 7, a 4E-BP1 GSK3 substrate including the amino acid sequence of SEQ ID No. 8, and a 4E-BP1 GSK3 substrate including the peptide encoded by the complement of a nucleic acid sequence that hybridizes under high stringency hybridization conditions to SEQ ID No. 9 where the encoded GSK3 substrate includes at least one GSK3 phosphorylation motif.

A commercial package can contain, for example, a 4E-BP1 polypeptide, or portion thereof, such as SEQ ID No. 7 or modification thereof, together with a GSK3α and/or GSK3β assay component.

A commercial package can contain, for example, a 4E-BP1 polypeptide, or portion thereof, such as SEQ ID No. 8 or modification thereof, together with a GSK3α and/or GSK3β assay component.

Exemplary assay components include an antibody that recognizes GSK3α and/or GSK3β, and a preparation containing GSK3α and/or GSK3β kinase activity, such as cells, cell lysates or purified enzyme material. Purified enzyme material can be derived from the full length enzyme or the catalytic domain of GSK3α and/or GSK3β enzymes. A commercial package also can contain one or more antibodies that recognize a 4E-BP1 GSK3 substrate polypeptide or portion thereof, in particular an antibody that recognizes a phosphorylated form of the 4E-BP1 polypeptide, or portion thereof, such as a polypeptide portion containing an amino acid(s) corresponding to Thr37 and/or Thr46 of the full length 4E-BP1 polypeptide.

The term "antibody" encompasses polyclonal antibodies, monoclonal antibodies (mAbs), chimeric antibodies, humanized antibodies, as well as antigen binding antibody fragments and molecules having functionality to bind a specified antigen.

The term "antibody" includes an intact immunoglobulin having four polypeptide chains, two heavy (H) chains and two light (L) chains linked by disulfide bonds. The term "antibody" also encompasses antibody fragments illustratively including, but not limited to, such fragments as an Fab fragment, an Fab' fragment, an F(ab')2 fragment, an Fd fragment, an Fv fragment, an scFv fragment, and a domain antibody (dAb).

Antibodies and antigen binding antibody fragments and methods for their generation are known in the art and are described in further detail, for instance, in Antibody Engineering, Kontermann, R. and Dübel, S. (Eds.), Springer, 2001; Harlow, E. and Lane, D., Antibodies: A Laboratory Manual, Cold Spring Harbor Laboratory Press, 1988; Ausubel, F. et al., (Eds.), Short Protocols in Molecular Biology, Wiley, 2002; J. D. Pound (Ed.) Immunochemical Protocols, Methods in Molecular Biology, Humana Press; 2nd ed., 1998; B. K. C. Lo (Ed.), Antibody Engineering: Methods and Protocols, Methods in Molecular Biology, Humana Press, 2003; and Kohler, G. and Milstein, C., Nature, 256:495-497 (1975).

An antibody included in embodiments of a commercial package includes a detectable label. In particular embodiments, the detectable label is a FRET donor which interacts via FRET with a FRET acceptor incorporated into a 4E-BP1 GSK3 substrate. An exemplary FRET donor is europium.

Other components, such as buffers, reaction mixtures, reagents for attaching tags to reaction components, detectable labels, instructions, a control kinase, a control substrate, and the like can be included. As is suitable for a particular assay format, any included antibodies can be modified with tags useful, for example, for detection and/or capture. Similarly, the 4E-BP-1 can be modified with one or more tags. Also provided herein is a composition that contains GSK3α and/or GSK3β and 4E-BP1 or a portion thereof. For particular uses as defined by the user, the GSK3α, GSK3β and/or 4E-BP1 can be in isolated form, or present with other components in a sample.

A specific example of a commercial package is one that includes a 4E-BP1 polypeptide portion corresponding to SEQ ID No. 7 or modification thereof, and one or more antibodies that recognize the 4E-BP1 polypeptide portion, of which at least one antibody recognizes the 4E-BP1 polypeptide portion phosphorylated at an amino acid corresponding to Thr37 and/or Thr46 of the full length 4E-BP1, and a sample containing GSK3α and/or GSK3β kinase activity. Another specific example of a commercial package is one that includes a 4E-BP1 polypeptide portion corresponding to SEQ ID No. 7 or modification thereof, a sample containing GSK3α and/or GSK3β kinase activity. Optionally one or more antibodies that recognize GSK3α and/or GSK3β and/or one or more antibodies that recognize the 4E-BP1 polypeptide portion can be included.

A specific example of a commercial package is one that includes a 4E-BP1 polypeptide portion corresponding to SEQ ID No. 8 or modification thereof, and one or more antibodies that recognize the 4E-BP1 polypeptide portion, of which at least one antibody recognizes the 4E-BP1 polypeptide portion phosphorylated at an amino acid corresponding to Thr37 and/or Thr46 of the full length 4E-BP1, and a sample containing GSK3α and/or GSK3β kinase activity. Another specific example of a commercial package is one that includes a 4E-BP1 polypeptide portion corresponding to SEQ ID No. 8 or modification thereof, a sample containing GSK3α and/or GSK3β kinase activity. Optionally one or more antibodies that recognize GSK3α and/or GSK3β and/or one or more antibodies that recognize the 4E-BP1 polypeptide portion can be included.

Embodiments described herein are illustrated in the following examples. These examples are provided for illustrative purposes and are not considered limitations on the scope of the invention.

EXAMPLE 1

This example describes an AlphaScreen® format phosphorylation assay, which was employed to demonstrate phosphorylation of full length 4E-BP1 by GSK3β (FIG. 1).

AlphaLISA is a bead-based proximity assay useful for studying biomolecular interactions. AlphaLISA assays contain two bead types: Donor beads and Acceptor beads. When target molecules are bound by both the Donor and Acceptor beads, the two beads are brought into proximity. Irradiation of the complexed reagents at 680 nm causes the generation of a flow of singlet oxygen by the Donor beads. This singlet oxygen induces an energy transfer cascade in the acceptor bead in proximity ($\leq$200 nm), ultimately producing a light signal at 615 nm. This signal is measured directly or as a concentration value based on a standard curve. When there is no binding, Donor and Acceptor beads are not in close proximity, singlet oxygen decays, and no signal is produced.

In the present example, the phosphorylation of full-length 4E-BP1 at position Thr37 and/or Thr46 was detected using a rabbit monoclonal antibody recognizing phosphorylated-4E-BP1 at one or both of these two positions. Donor beads conjugated with a nickel chelate were used for the selective capture of the polyhistidine tag present on the full length 4E-BP1. The Acceptor beads were conjugated with an antibody that recognizes rabbit immunoglobulins. In the kinase assay, GSK3β (at 20 nM) was incubated with the His-tagged 4E-BP1 protein in the presence of ATP. After completion of the kinase reaction, the anti-phosphorylated-4E-BP1 antibody (Thr37/46), pre-coupled to the Acceptor beads was added. Lastly, nickel chelate-Donor beads were added to the reaction for detection. In the reaction mixture, a "molecular sandwich" comprised of [nickel-chelate Donor beads]-[phosphorylated-polyhistidine tagged-4E-BP1 protein]-[rabbit anti-phospho-4E-BP1 immunoglobulin]-[anti-rabbit immunoglobulin-coupled Acceptor beads] was formed. After irradiation at 680 nm, the proximity of Donor and Acceptor beads allowed the production of a signal at 615 nm. Since GSK3β activity requires the presence of adenosine triphosphate (ATP), this kinase assay was performed in the presence and absence of ATP. Signal to background ratios were calculated by dividing signal in the +ATP well by signal in the −ATP wells.

A summary of reaction conditions is presented below:
GSK3β kinase (Curia Biosciences): 20 nM
His-4E-BP1 (full-length) (Santa Cruz #SC-4251): 100 nM
ATP: 100 μM
Reaction time: 4 h
Anti-p-4E-BP1: 1 nM
AlphaLISA® anti-Rabbit Acceptor Beads: 5, 10 or 20 μg/mL
60 min at 23° C.
Ni chelate Donor beads: 20 or 40 μg/mL
60 min at 23° C.
Results of this assay are shown in Table I below:

| Acceptor/<br>Donor<br>beads (μg/mL) | +100 μM ATP | | | −ATP | | | |
|---|---|---|---|---|---|---|---|
| | Y1 | Y2 | Y3 | Y1 | Y2 | Y3 | S/B |
| 5/20 | 7587 | 7824 | 7657 | 692 | 810 | 911 | 9.6 |
| 10/20 | 11851 | 12175 | 11443 | 1364 | 1362 | 1499 | 8.4 |
| 20/20 | 23312 | 24088 | 23736 | 2683 | 2655 | 3223 | 8.3 |
| 5/40 | 8396 | 8324 | 8333 | 449 | 538 | 512 | 16.7 |
| 10/40 | 13347 | 13851 | 13490 | 1003 | 964 | 977 | 13.8 |
| 20/40 | 27834 | 27561 | 27576 | 2027 | 1864 | 2007 | 14.1 |

Assays in this example were performed in triplicate and in Table I, columns Y1, Y2 and Y3 separately show data from each individual assay of the triplicates performed in the presence or absence of ATP. The column labeled S/B shows signal/background (S/B) data, where the signal is the average of Y1, Y2 and Y3 where the assays are performed in the presence of ATP (+ATP), and the background is the average of Y1, Y2 and Y3 where the assays are performed in the absence of ATP (−ATP).

FIG. 1 is a graph showing results of the assay described in this example and demonstrates GSK3β phosphorylation activity on full-length 4E-BP1.

EXAMPLE 2

This example describes an LANCE® Ultra format assay, which was employed to demonstrate phosphorylation of a 4E-BP1-derived peptide by GSK3α and GSK3β in the presence of ATP.

LANCE® Ultra assays are based on time-resolved fluorescence resonance energy transfer (TR-FRET). They use a proprietary europium chelate donor dye, W-1024 (Eu), with ULight®, a small molecular weight acceptor dye with a red fluorescent emission. In kinase assays, the binding of a Eu-labeled anti-phospho-substrate antibody to the phosphorylated ULight-labeled substrate brings donor and acceptor dye molecules into proximity. After irradiation of the kinase reaction at 320 or 340 nm, the energy from the Eu donor is transferred to the ULight acceptor dye which, in turn, generates light at 665 nm. The intensity of the light emission is proportional to the level of ULight-substrate phosphorylation.

In this example, a 4E-BP1 fragment peptide GSK3 substrate including the amino acid sequence PGDYSTTPG-GTLFSTTPGGTR (SEQ ID No. 7) is used. The peptide of SEQ ID No. 7 is modified by addition of three amino acids at both the N- and C-termini to facilitate solubilizing the peptide and labeling of the peptide with a FRET acceptor label. The modified 4E-BP1-derived peptide GSK3 substrate has the amino acid sequence CDDPGDYSTTPGGTLFSTTPG-GTRDYD (SEQ ID No. 8) and is synthesized by standard peptide synthetic techniques. Thr37/Thr46 of full-length 4E-BP1 corresponds to Thr10/Thr19 in SEQ ID No.8. The peptide is tagged at the N-terminal cysteine with the FRET acceptor label ULight and is non-primed for use in this example assay.

Experiments were performed to assess phosphorylation of 4E-BP1 fragment peptide GSK3 substrate by GSK3α and GSK3β. For GSK3β, the kinase was provided in three amounts (0.2, 2 and 5 nM) and incubated with the 4E-BP1 fragment peptide GSK3 substrate labeled with a ULight tag at a concentration of 50 nM.

Anti-phosphorylated-4E-BP1 (Thr37/Thr46) antibody labeled with a Europium chelate was used at final concentration of 2 nM to bind to resulting 4E-BP1-derived peptide phosphorylated at amino acid residues Thr37 and/or Thr46. Proximity of the ULight dye and Europium chelate resulted in a LANCE signal, which was measured at 665 nm. This kinase assay was performed in the presence of 100 µM ATP and in the absence of ATP. Signal to background ratios were calculated by dividing signal in the +ATP well by signal in the −ATP wells.

This example also shows activities of various preparations of GSK3β from different vendors including Carna Biosciences, ProQinase. It was noted that: GSK3β from Carna at 2 to 5 nM provided the higher signal and best performance (signal to background ratio of ~37), with this set up.

Results of this assay are shown in Table II below:

EXAMPLE 3

An assay using conditions similar to those described in Example 2 was performed to assess phosphorylation of 4E-BP1-derived peptide by both GSK3α and GSK3β. A concentration of 20 nM GSK3 enzymes was used for this assay. A 4E-BP1 fragment peptide GSK3 substrate CDDPGDYST-TPGGTLFSTTPGGTRDYD (SEQ ID No. 8) is used. The peptide is tagged at the N-terminal cysteine with the FRET acceptor label ULight and is non-primed for use in this example assay. Results of this assay are shown in Table III below:

| Kinase | S/B |
|---|---|
| GSK3α (Carna) n = 1 | 35.7 |
| GSK3α (Carna) n = 2 | 33.2 |
| GSK3β (Carna) n = 1 | 35.9 |
| GSK3β (Carna) n = 2 | 35.8 |
| GSK3β (ProQinase) n = 1 | 36.7 |
| GSK3β (ProQinase) n = 2 | 30.7 |

Figure 3:
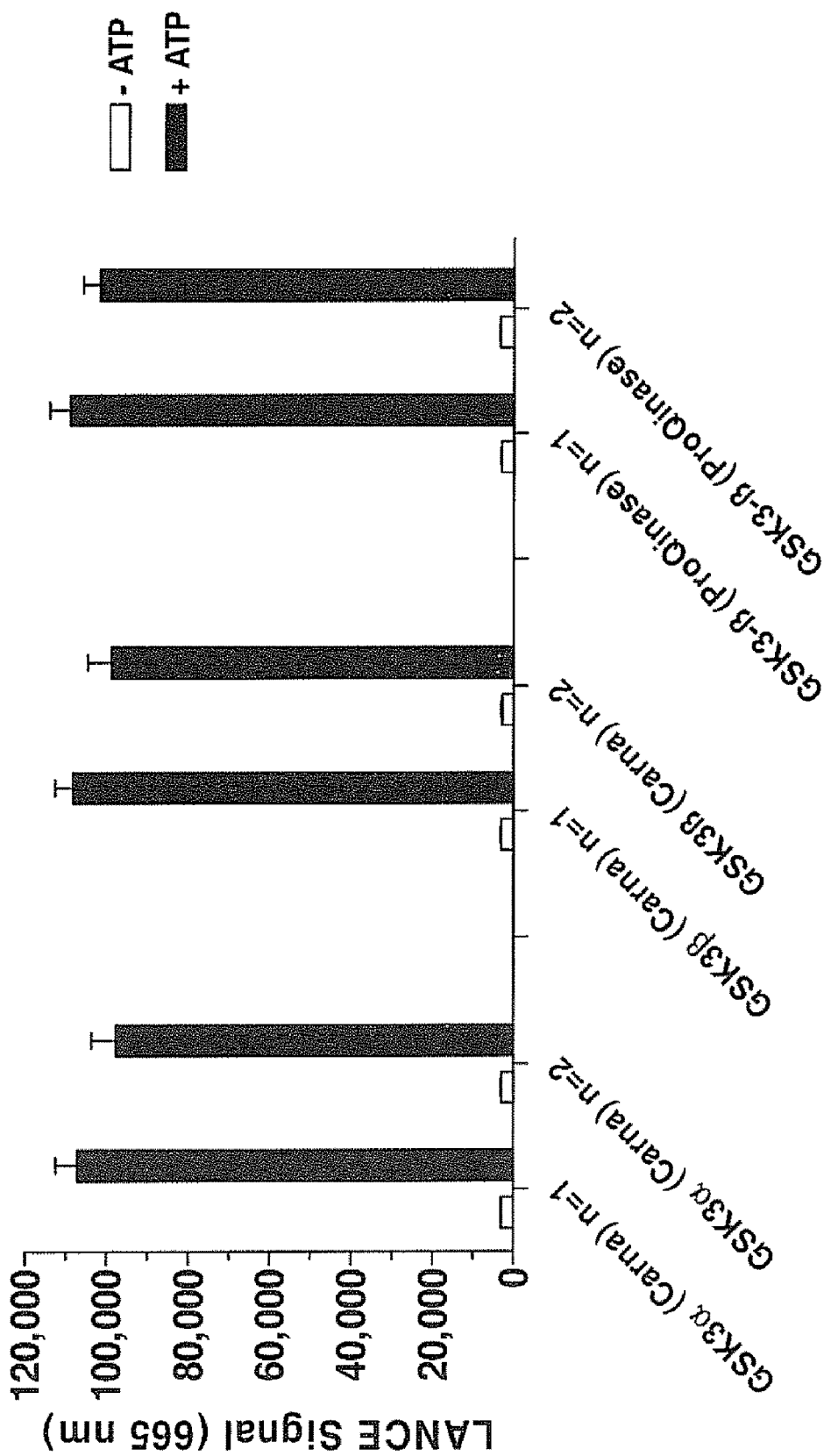
FIG. 3 is a graph showing the results of a kinase assay using time-resolved fluorescence resonance energy transfer to detect phosphorylation of a 4E-BP1-derived peptide by GSK3α or GSK3β. The 4E-BP1-derived peptide substrate of SEQ ID No. 7 was used, modified by addition of three amino acids at both the N- and C-termini to facilitate solubilizing the peptide and labeling of the peptide with a FRET acceptor label. For this assay, GSK3α or GSK3β as indicated on the x-axis was incubated with non-primed FRET-acceptor labeled 4E-BP1-derived peptide in the presence or absence of ATP. Anti-phosphorylated-4E-BP1 antibody (Thr37/46) labeled with a FRET donor is added and upon irradiation, the proximity of the FRET donor and FRET acceptor produce a signal, shown on the y-axis. The assays were performed in duplicate, the results of the first assay labeled n=1 and the results of the second assay labeled n=2.

FIG. 3 is a graph showing results of the assay described in this example and demonstrates GSK3α and GSK3β phosphorylation activity on a FRET acceptor labeled-4E-BP1 fragment peptide GSK substrate.

EXAMPLE 4

This example describes assays demonstrating that GSK3β activity on a 4E-BP1 GSK3 substrate is inhibited by kenpaullone and SB216763, two specific protein kinase inhibitors.

In a first assay using inhibitor SB216763 at various concentrations, reaction conditions used were:
Kinase reaction: 60 min
GSK3β kinase (Carna Biosciences): 2 nM
ATP: 10 µM

|  |  | +100 µM ATP | | | −ATP | | | |
|---|---|---|---|---|---|---|---|---|
| Supplier | GSK3β (nM) | Y1 | Y2 | Y3 | Y1 | Y2 | Y3 | S/B |
| Carna | 5 | ~~139261~~ 113695 | 113695 | 112092 | 3403 | 2908 | 2633 | 37.9 |
| | 2 | 101565 | 104701 | 104417 | 2910 | 2765 | 2813 | 36.6 |
| | 0.2 | 24209 | 25149 | 23739 | 2799 | 2782 | 2827 | 8.7 |
| ProQinase | 5 | 56668 | 58291 | 54942 | 2927 | 2775 | 2754 | 20.1 |
| | 2 | 24126 | 24697 | 22814 | 2694 | 2693 | 2663 | 8.9 |
| | 0.2 | 3364 | 3554 | 3592 | 2919 | 2804 | 2787 | 1.2 |

Assays in this example were performed in triplicate and in Table I. columns Y1, Y2 and Y3 separately show data from each individual assay of the triplicates performed in the presence or absence of ATP. The column labeled S/B shows signal/background (S/B) data, where the signal is the average of Y1,Y2 and Y3 where the assays are performed in the presence of ATP (+ATP), and the background is the average of Y1, Y2 and Y3 where the assays are performed in the absence of ATP (−ATP).

Figure 2:
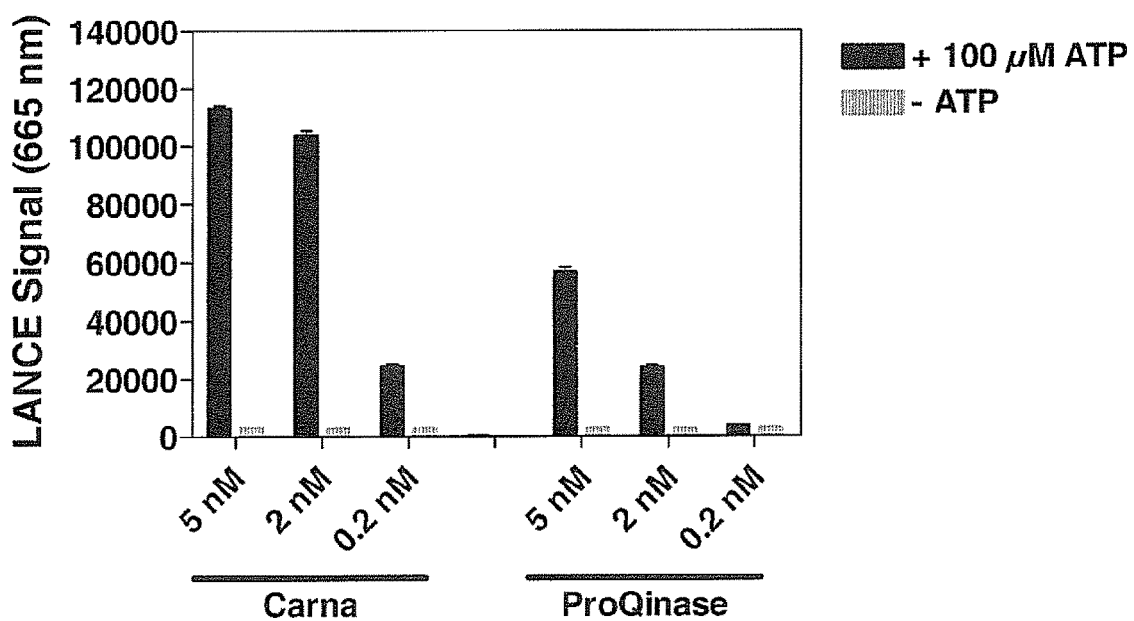
FIG. 2 is a graph showing the results of a kinase assay using time-resolved fluorescence resonance energy transfer to detect phosphorylation of a 4E-BP1derived peptide by GSK3β. For this assay, GSK3β from two commercial sources, Carna Biosciences (Carna) and ProQuinase, in amounts indicated on the x-axis was incubated with non-primed FRET-acceptor labeled 4E-BP1-derived peptide in the presence or absence of ATP. Anti-phosphorylated-4E-BP1 antibody (Thr37/46) labeled with a FRET donor is added and upon irradiation, the proximity of the FRET donor and PRET acceptor produce a signal, shown on the y-axis.

FIG. 2 is a graph showing results of the assay described in this example and demonstrates GSK3β phosphorylation activity on a FRET acceptor labeled-4E-BP1 fragment peptide GSK substrate.

ULight-4E-BP1: 50 nM
Eu-α-P-4E-BP1: 2 nM
DMSO 1%

Figure 4A:
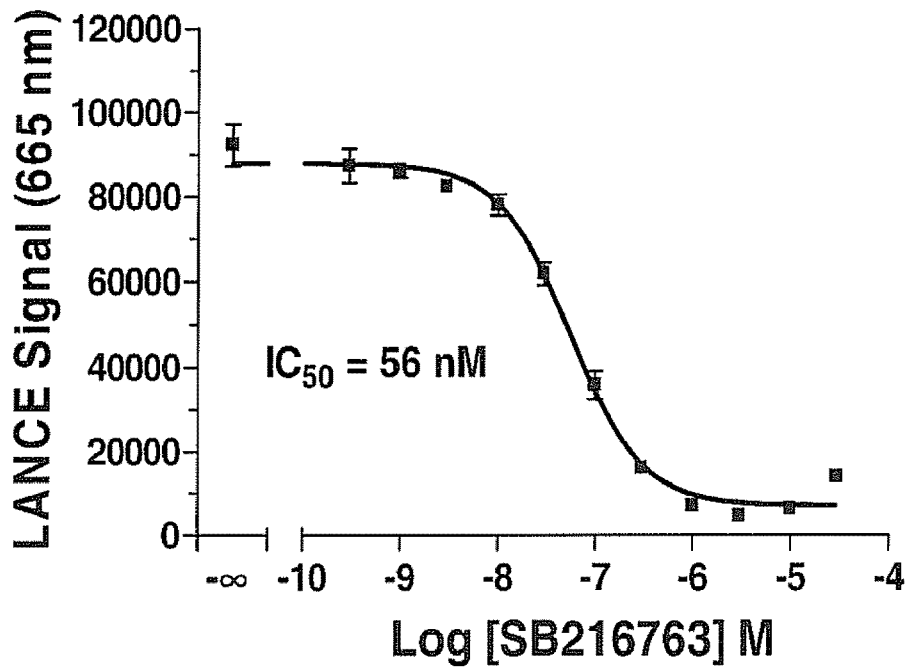
FIG. 4A is a graph showing the results of a kinase assay using time-resolved fluorescence resonance energy transfer to detect phosphorylation of a 4E-BP1-derived peptide by GSK3β, if any, in the presence of an inhibitor of GSK3β, SB216763. For this assay, GSK3β was incubated with non-primed FRET-acceptor labeled 4E-BP1-derived peptide in the presence of ATP and various concentrations of SB216763 indicated on the x-axis. Anti-phosphorylated-4E-BP1 antibody (Thr37/46) labeled with a FRET donor is added and upon irradiation, the proximity of the FRET donor and FRET acceptor produce a signal, shown on the y-axis. The 4E-BP1-derived peptide substrate of SEQ ID No. 7 was used, modified by addition of three amino acids at both the N- and C-termini to facilitate solubilizing the peptide and labeling of the peptide with a FRET acceptor label.

FIG. 4A is a graph showing results of the assay using inhibitor SB216763.

A second assay using inhibitor kenpaullone at various concentrations is performed and reaction conditions used were:
Kinase reaction: 60 min
GSK3β kinase (Carna Biosciences): 2 nM
ATP: 10 µM
ULight-4E-BP1: 50 nM
Eu-α-P-4E-BP1: 2 nM
DMSO 1%

Figure 4B:
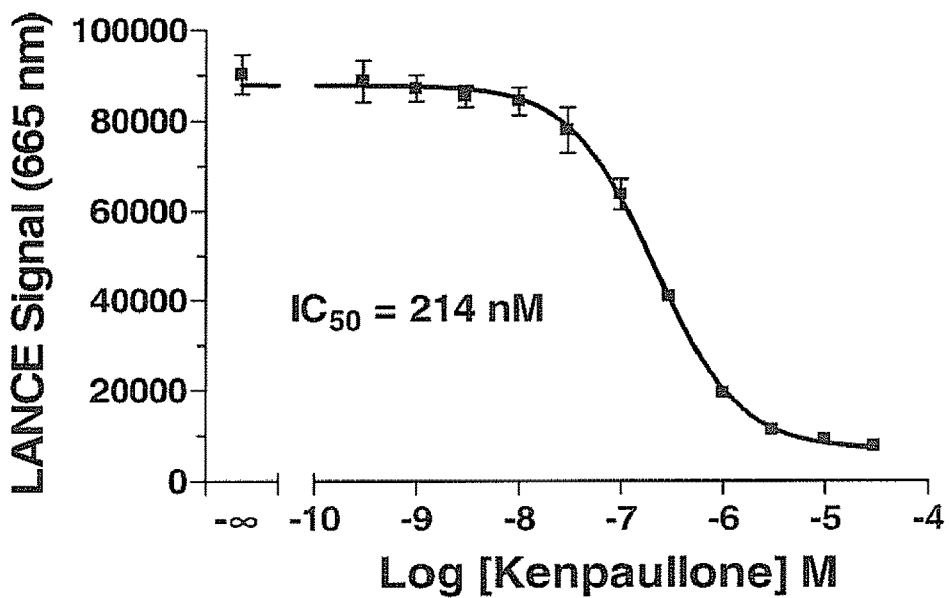
FIG. 4B is a graph showing the results of a kinase assay using time-resolved fluorescence resonance energy transfer to detect phosphorylation of a 4E-BP1-derived peptide by GSK3β, if any, in the presence of an inhibitor of GSK3β, kenpaullone. For this assay, GSK3β was incubated with non-primed FRET-acceptor labeled 4E-BP1-derived peptide in the presence of ATP and various concentrations of kenpaullone indicated on the x-axis. Anti-phosphorylated-4E-BP1 antibody (Thr37/46) labeled with a FRET donor is added and upon irradiation, the proximity of the FRET donor and FRET acceptor produce a signal, shown on the y-axis The 4E-BP1-derived peptide substrate of SEQ ID No. 7 was used, modified by addition of three amino acids at both the N- and C-termini to facilitate solubilizing the peptide and labeling of the peptide with a FRET acceptor label.

FIG. 4B is a graph showing results of the assay using inhibitor kenpaullone.

Since it has been reported the two inhibitors strongly inhibit GSK3 enzyme while having distinct specificities for other kinases [see Bain et al. (2007), Biochem J. 408:297-315], this experiment demonstrates that the observed phosphorylation is specifically due to GSK3β and not to a contaminating activity that could have been present in the commercial enzyme preparation. Importantly, the degree of inhibition obtained with both inhibitors is in line with those reported on the literature (at the low μM level, >95% inhibition was obtained) [Bain et al. (2007), Biochem J. 408:297-315].

Sequences

Glycogen synthase kinase-3 alpha Homo sapiens
SEQ ID No. 1
MSGGGPSGGGPGGSGRARTSSFAEPGGGGGGGGGPGGSASGPGGTGG
GKASVGAMGGGVGASSSGGGPGGSGGGGSGGPGAGTSFPPPGVKLGRD
SGKVTTVVATLGQGPERSQEVAYTDIKVIGNGSFGVVYQARLAETREL
VAIKKVLQDKRFKNRELQIMRKLDHCNIVRLRYFFYSSGEKKDELYLN
LVLEYVPETVYRVARHFTKAKLTIPILYVKVYMYQLFRSLAYEFISQG
VCIARDIKPQNLLVDPDTAVLKLCDFGSAKQLVRGEPNVSYICSRYYR
APELIFGATDYTSSIDVWSAGCVLAELLLGQPIFPGDSGVDQLVEITK
VLGTPTREQIREMNPNYTEFKFPQIKAHPWTKVFKSRTPPEAIALCSS
LLEYTPSSRLSPLEACAHSFFDELRCLGTQLPNNRPLPPLFNFSAGEL
SIQPSLNAILIPPHLRSPAGTTTLTPSSQALTETPTSSDWQSTDATPT
LTNSS Glycogen synthase kinase-3 alpha Homo sapiens
SEQ ID No. 2
ATGAGCGGCGGCGGGCCTTCGGGAGGCGGCCCTGGGGGCTCGGGCAGG
GCGCGGACTAGCTCGTTCGCGGGCCCGGCGGCGGAGGCGGAGGAGGCG
GCGGCGGCCCCGGAGGCTCGGCCTCCGGCCCAGGCGGCACCGGCGGCG
GAAAGGCATCTGTCGGGGCCATGGGTGGGGCGTCGGGGCCTCGAGCT
CCGGGGGTGGACCCGGCGGCAGCGGCGGAGGAGGCAGCGGAGGCCCCG
GCGCAGGCACTAGCTTCCCGCCGCCCGGGGTGAAGCTGGGCCGTGACA
GCGGGAAGGTGACCACAGTCGTAGCCACTCTAGGCCAAGGCCCAGAGC
GCTCCCAAGAAGTGGCTTACACGGACATCAAAGTGATTGGCAATGGCT
CATTTGGGGTCGTGTACCAGGCACGGCTGGCAGAGACCAGGGAACTAG
TCGCCATCAAGAAGGTTCTCCAGGACAAGAGGTTCAAGAACCGAGAGC
TGCAGATCATGCGTAAGCTGGACCACTGCAATATTGTGAGGCTGAGAT
ACTTTTTCTACTCCAGTGGCGAGAAGAAAGACGAGCTTTACCTAAATC
TGGTGCTGGAATATGTGCCCGAGACAGTGTACCGGGTGGCCCGCCACT
TCACCAAGGCCAAGTTGACCATCCCTATCCTCTATGTCAAGGTGTACA
TGTACCAGCTCTTCCGCAGCTTGGCCTACATCCACTCCCAGGGCGTGT
GTCACCGCGACATCAAGCCCCAGAACCTGCTGGTGGACCCTGACACTG
CTGTCCTCAAGCTCTGCGATTTTGGCAGTGCAAAGCAGTTGGTCGAG
GGGAGCCCAATGTCTCCTACATCTGTTCTCGCTACTACCGGGCCCCAG
AGCTCATCTTTGGAGCCACTGATTACACCTCATCCATCGATGTTTGGT
CAGCTGGCTGTGTACTGGCAGAGCTCCTCTTGGGCCAGCCCATCTTCC
CTGGGGACAGTGGGGTGGACCAGCTGGTGGAGATCATCAAGGTGCTGG
GAACACCAACCCGGGAACAAATCCGAGAGATGAACCCCAACTACACGG
AGTTCAAGTTCCCTCAGATTAAAGCTCACCCCTGGACAAAGGTGTTCA
AATCTCGAACGCCGCCAGAGGCCATCGCGCTCTGCTCTAGCCTGCTGG
AGTACACCCCATCCTCAAGGCTCTCCCCACTAGAGGCCTGTGCGCACA
GCTTCTTTGATGAACTGCGATGTCTGGGAACCCAGCTGCCTAACAACC
GCCCACTTCCCCCTCTCTTCAACTTCAGTGCTGGTGAACTCTCCATCC
AACCGTCTCTCAACGCCATTCTTATCCCTCCTCACTTGAGGTCCCCAG
CGGGCACTACCACCCTCACCCCGTCCTCACAAGCTTTAACTGAGACTC
CGACCAGCTCAGACTGGCAGTCGACCGATGCCACACCTACCCTCACTA
ACTCCTCCTGA Glycogen synthase kinase-3 beta Homo sapiens
SEQ ID No. 3
MSGRPRTTSFAESCKPVQQPSAFGSMKVSRDICDGSKVTTVVATPGQG
PDRPQEVSYTDTKVIGNGSFGVVYQAKLCDSGELVAIKKVLQDKRFKN
RELQIMRKLDHCNIVRLRYFFYSSGEKKDEVYLNLVLDYVPETVYRVA
RHYSRAKQTLPVIYVKLYMYQLFRSLAYIHSFGICHRDIKPQNLLLDP
DTAVLKLCDFGSAKQLVRGEPNVSYICSRYYRAPEUFGATDYTSSIDV
WSAGCVLAELLLGQPIFPGDSGVDQLVEIIKVLGTPTREQIREMNPNY
TEFKFPQIKAEIPWTKVFRPRTPPEAIALCSRLLEYTPTARLTPLEAC
AHSFFDELRDPNVKLPNGRDTPALFNFTTQELSSNPPLATILIPPHAR
IQAAASTPTNATAASDANTGDRGQTNNAASASASNST Glycogen synthase kinase-3 beta Homo sapiens
SEQ ID No. 4
ATGTCAGGGCGGCCCAGAACCACCTCCTTTGCGGAGAGCTGCAAGCCG
GTGCAGCAGCCTTCAGCTTTTGGCAGCATGAAAGTTAGCAGAGACAAG
GACGGCAGCAAGGTGACAACAGTGGTGGCAACTCCTGGGCAGGGTCCA
GACAGGCCACAAGAAGTCAGCTATACAGACACTAAAGTGATTGGAAAT
GGATCATTTGGTGTGGTATATCAAGCCAAACTTTGTGATTCAGGAGAA
CTGGTCGCCATCAAGAAAGTATTGCAGGACAAGAGATTTAAGAATCGA
GAGCTCCAGATCATGAGAAAGCTAGATCACTGTAACATAGTCCGATTG
CGTTATTTCTTCTACTCCAGTGGTGAGAAGAAAGATGAGGTCTATCTT
AATCTGGTGCTGGACTATGTTCCGGAAACAGTATACAGAGTTGCCAGA
CACTATAGTCGAGCCAAACAGACGCTCCCTGTGATTTATGTCAAGTTG
TATATGTATCAGCTGTTCCGAAGTTTAGCCTATATCCATTCCTTTGGA
ATCTGCCATCGGGATATTAAACCGCAGAACCTCTTGTTGGATCCTGAT
ACTGCTGTATTAAAACTCTGTGACTTTGGAAGTGCAAAGCAGCTGGTC
CGAGGAGAACCCAATGTTTCGTATATCTGTTCTCGGTACTATAGGGCA
CCAGAGTTGATCTTTGGAGCCACTGATTATACCTCTAGTATAGATGTA
TGGTCTGCTGGCTGTGTGTTGGCTGAGCTGTTACTAGGACAACCAATA
TTTCCAGGGGATAGTGGTGTGGATCAGTTGGTAGAAATAATCAAGGTC
CTGGGAACTCCAACAAGGGAGCAAATCAGAGAAATGAACCCAAACTAC

ACAGAATTTAAATTCCCTCAAATTAAGGCACATCCTTGGACTAAGGTC

TTCCGACCCCGAACTCCACCGGAGGCAATTGCACTGTGTAGCCGTCTG

CTGGAGTATACACCAACTGCCCGACTAACACCACTGGAAGCTTGTGCA

CATTCATTTTTTGATGAATTACGGGACCCAAATGTCAAACATCCAAAT

GGGCGAGACACACCTGCACTCTTCAACTTCACCACTCAAGAACTGTCA

AGTAATCCACCTCTGGCTACCATCCTTATTCCTCCTCATGCTCGGATT

CAAGCAGCTGCTTCAACCCCCACAAATGCCACAGCAGCGTCAGATGCT

AATACTGGAGACCGTGGACAGACCAATAATGCTGCTTCTGCATCAGCT

TCCAACTCCACCTGA

Eukaryotic translation initiation factor
4E-binding protein 1 Homo sapiens
SEQ ID No. 5
MSGGSSCSQTPSRAIPATRRVVLGDGVQLPPGDYSTTPGGTLFSTTPG

GTRIIYDRKFLMECRNSPVTKTPPRDLPTIPGVTSPSSDEPPMEASQS

HLRNSPEDKRAGGEESQFEMDI

Homo sapiens eukaryotic translation initiation
factor 4E-binding protein 1
SEQ ID No. 6
ATGTCCGGGGGCAGCAGCTGCAGCCAGACCCCAAGCCGGGCCATCCCC

GCCACTCGCCGGTGGTGCTCGGCGACGGCGTGCAGCTCCCGCCCGGG

GACTACAGCACGACCCCCGGCGGCACGCTCTTCAGCACCACCCCGGGA

GGTACCAGGATCATCTATGACCGGAAATTCCTGATGGAGTGTCGGAAC

TCACCTGTGACCAAAACACCCCCAAGGGATCTGCCCACCATTCCGGGG

GTCACCAGCCCTTCCAGTGATGAGCCCCCCATGGAAGCCAGCCAGAGC

CACCTGCGCAATAGCCCAGAAGATAAGCGGGCGGGCGGTGAAGAGTCA

CAGTTTGAGATGGACATTTAA

Fragment of Homo sapiens Eukaryotic translation
initiation factor 4E-binding protein 1
SEQ ID No. 7
PGDYSTTPGGTLFSTTPGGTR Artificial 4E-BP1 PGK3 substrate
SEQ ID No. 8
CDDPGDYSTTPGGTLFSTTPGGTRDYD Nucleic acid encoding fragment of Homo sapiens
Eukaryotic translation initiation factor 4E-
binding protein 1
SEQ ID No. 9
CCCGGGGACTACAGCACGACCCCCGGCGGCACGCTCTTCAGCACCACC

CCGGGAGGTACCAGG

Any patents or publications mentioned in this specification are incorporated herein by reference to the same extent as if each individual publication is specifically and individually indicated to be incorporated by reference. U.S. Provisional Patent Application Ser. No. 61/246,468, filed Sep. 28, 2009, is incorporated herein by reference in its entirety.

The compositions, methods and commercial packages described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. An in vitro method of identifying a glycogen synthase kinase 3 (GSK3) modulator, comprising contacting a GSK3 and a 4E-BP1-derived GSK3 substrate under GSK3 kinase activity reaction conditions, in the presence and absence of a test substance;
wherein the GSK3 comprises a protein selected from the group consisting of:
(i) the GSK3 of SEQ ID No: 1 or 3,
(ii) a protein consisting of a sequence at least 95% identical to SEQ ID NO: 1 or 3 and functional to phosphorylate SEQ ID NO: 5, on residues $Thr^{37}$ and/or $Thr^{46}$, and
(iii) a GSK3 encoded by the complement of a nucleic acid which hybridizes to SEQ ID No: 2 or 4 under highly stringent hybridization conditions comprising hybridization in a solution containing 6×SSC, 5× Denhardt's solution, 30% formamide, and 100 micrograms/ml denatured salmon sperm at 37° C. overnight, followed by washing in a solution of 0.1×SSC and 0.1% SDS at 65° C. for 15 minutes and functional to phosphorylate SEQ ID NO: 5, on residues $Thr^{37}$ and/or $Thr^{46}$;
wherein the 4E-BP1-derived GSK3 substrate comprises a non-primed protein selected from the group consisting of:
(a) the polypeptide of SEQ ID No. 5,
(b) a polypeptide consisting of a sequence at least 90% identical to SEQ ID NO: 5 and having at least one Thr-X-X-X-Thr motif, where each X is an independently selected amino acid, and each of said at least one motif can be phosphorylated by the protein of SEQ ID NO: 1 or 3,
(c) the polypeptide of SEQ ID No. 7,
(d) a polypeptide consisting of a sequence at least 90% identical to SEQ ID NO: 7 and having at least one Thr-X-X-X-Thr motif, where each X is an independently selected amino acid, and each of said at least one motif can be phosphorylated by the protein of SEQ ID NO: 1 or 3,
(e) the polypeptide of SEQ ID No. 8,
(f) a polypeptide consisting of a sequence at least 90% identical to SEQ ID NO: 8 and having at least one Thr-X-X-X-Thr motif, where each X is an independently selected amino acid, and each of said at least one motif can be phosphorylated by the protein of SEQ ID NO: 1 or 3,
(g) a polypeptide consisting of a sequence encoded by the complement of a nucleic acid which hybridizes to SEQ ID No: 6 under highly stringent hybridization conditions comprising hybridization in a solution containing 6×SSC, 5× Denhardt's solution, 30% formamide, and 100 micrograms/ml denatured salmon sperm at 37° C. overnight, followed by washing in a solution of 0.1×SSC and 0.1% SDS at 65° C. for 15 minutes, said polypeptide having at least one motif, Thr-X-X-X-Thr, where each X is an independently selected amino acid, and each of said at least one motif can be phosphorylated by the protein of SEQ ID NO: 1 or 3, and (h) a fragment of a polypeptide consisting of a sequence at least 90% identical to SEQ ID NO: 5 and having at least one Thr-X-X-X-Thr motif, where each X is an independently selected amino acid, and each of said at least one motif can be phosphorylated by the protein of SEQ ID NO: 1 or 3;

wherein the method detects phosphorylation of the 4E-BP1-derived GSK3 substrate by the GSK3 polypeptide and;

wherein changes in the phosphorylation of the 4E-BP1-derived GSK3 substrate by the GSK3 polypeptide in the presence, compared to the absence, of the test substance identifies the test substance as a GSK3 modulator.

2. The method of identifying a GSK3 modulator of claim 1, wherein the GSK3 comprises a protein having at least 96% identity to SEQ ID NO: 1 or SEQ ID NO:3 and the protein is functional to phosphorylate SEQ ID NO: 5, on residues $Thr^{37}$ and/or $Thr^{46}$.

3. The method of identifying a GSK3 modulator of claim 1, wherein the 4E-BP 1-derived GSK3 substrate comprises a protein having at least 91%, identity to SEQ ID NO: 5, SEQ ID NO: 7, or SEQ ID NO: 8 and having at least one GSK3 phosphorylation motif Thr-X-X-X-Thr, wherein each X is an independently selected amino acid, and each of said at least one motif can be phosphorylated by the protein of SEQ ID NO: 1 or 3.

4. The method of identifying a GSK3 modulator of claim 1, wherein the 4E-BP1-derived GSK3 substrate comprises a variant of a fragment of SEQ ID No. 5, wherein said variant fragment has at least 10 amino acids, has at least 91% to the corresponding fragment of SEQ ID NO: 5, includes at least one Thr-X-X-X-Thr motif, wherein each X is an independently selected amino acid, and wherein each of said at least one motif can be phosphorylated by the protein of SEQ ID NO: 1 or 3.

* * * * *